(12) United States Patent
Turco

(10) Patent No.: US 10,359,433 B2
(45) Date of Patent: Jul. 23, 2019

(54) BAG3 AS BIOCHEMICAL SERUM AND TISSUE MARKER

(71) Applicant: BIOUNIVERSA S.R.L., Fisciano (SA) (IT)

(72) Inventor: Maria Caterina Turco, Avellino (IT)

(73) Assignee: BIOUNIVERSA S.R.L., Fisciano (SA) (IT)

(*) Notice: Subject to any disclaimer, the term of this patent is extended or adjusted under 35 U.S.C. 154(b) by 282 days.

(21) Appl. No.: 14/572,654

(22) Filed: Dec. 16, 2014

(65) Prior Publication Data

US 2015/0147767 A1  May 28, 2015

Related U.S. Application Data

(63) Continuation of application No. PCT/EP2013/061976, filed on Jun. 11, 2013.

(30) Foreign Application Priority Data

Jun. 19, 2012 (EP) .................................. 12172531

(51) Int. Cl.
  *G01N 33/53* (2006.01)
  *G01N 33/68* (2006.01)
  *C07K 16/18* (2006.01)
  *C12Q 1/6883* (2018.01)
  *C12Q 1/6886* (2018.01)
  *G01N 33/574* (2006.01)
  *C07K 14/47* (2006.01)

(52) U.S. Cl.
  CPC ......... *G01N 33/6893* (2013.01); *C07K 14/47* (2013.01); *C07K 16/18* (2013.01); *C12Q 1/6883* (2013.01); *C12Q 1/6886* (2013.01); *G01N 33/57407* (2013.01); *G01N 33/57438* (2013.01); *G01N 33/57496* (2013.01); *G01N 33/6887* (2013.01); *C07K 2317/21* (2013.01); *C12Q 2600/118* (2013.01); *C12Q 2600/158* (2013.01); *G01N 2333/47* (2013.01); *G01N 2800/324* (2013.01); *G01N 2800/325* (2013.01); *G01N 2800/7095* (2013.01)

(58) Field of Classification Search
  CPC ......... G01N 33/6893; G01N 33/57496; G01N 33/6887; G01N 33/57438; G01N 33/57407; G01N 2333/47; G01N 2800/7095; G01N 2800/324; G01N 2800/325; C12Q 1/6886; C12Q 1/6883; C12Q 2600/118; C12Q 2600/158; C07K 2317/21; C07K 14/47; C07K 16/18
  See application file for complete search history.

(56) References Cited

U.S. PATENT DOCUMENTS

| 5,652,223 | A | * | 7/1997 | Kohn | ...................... | C12N 15/52 |
|---|---|---|---|---|---|---|
| | | | | | | 435/320.1 |
| 7,537,760 | B2 | * | 5/2009 | Leone | .............. | G01N 33/57426 |
| | | | | | | 424/139.1 |
| 2003/0068664 | A1 | * | 4/2003 | Albitar | ................. | G01N 33/564 |
| | | | | | | 435/7.92 |
| 2003/0073623 | A1 | | 4/2003 | Drmanac et al. | | |
| 2008/0166733 | A1 | * | 7/2008 | Reed | ..................... | C12Q 1/6886 |
| | | | | | | 435/6.12 |
| 2009/0047689 | A1 | * | 2/2009 | Kolman | .......... | G01N 33/57423 |
| | | | | | | 435/7.23 |
| 2013/0331283 | A1 | * | 12/2013 | McAndrew | .......... | G01N 33/564 |
| | | | | | | 506/9 |

FOREIGN PATENT DOCUMENTS

| EP | 1323733 A1 | | 2/2003 | | |
|---|---|---|---|---|---|
| WO | WO 03/055908 | * | 3/2003 | ............. | C07K 14/47 |
| WO | 2011/044927 A1 | | 4/2011 | | |
| WO | 2011067377 A1 | | 6/2011 | | |
| WO | 2012049664 A2 | | 4/2012 | | |

OTHER PUBLICATIONS

Mayeux et al., Biomarkers: Potential Uses and Limitations, NeuroRx, 1, (2004), p. 182-188.*
Selcen et al., Annals of Neurology Jan. 2009;vol. 65, No. 1, pp. 83-89.*
Arimura et al., Num Mutat 2011;32:1481-1491.*
Festa M, et al. "BAG3 Protein Is Overexpressed in Human Glioblastoma and Is a Potential Target for Therapy." The American Journal of Pathology; vol. 178.6. Jun. 2011; pp. 2504-2512. PMC.
Chen HY, et al. "Bag3 Gene Expression in Chronic Lymphocytic Leukemia and Its Association with Patients' Prognosis." Journal of Experimental Hematology / Chinese Association of Pathophysiology Aug. 2010; vol. 18(4); pp. 838-842.
Pagliuca MG, et al. "Regulation by heavy metals and temperature of the human BAG-3 gene, a modulator of Hsp70 activity." FEBS Letters. Apr. 24, 2003;541(1-3); pp. 11-15.
Liao Q, et al. "The anti-apoptotic protein BAG-3 is overexpressed in pancreatic cancer and induced by heat stress in pancreatic cancer cell lines." FEBS Letters. Aug. 17, 2001;503(2-3); pp. 151-157.
Fontanella B, et al. "The co-chaperone BAG3 interacts with the cytosolic chaperonin CCT: new hints for actin folding." The International Journal of Biochemistry & Cell Biology. May 2010; vol. 42(5): pp. 641-650.

(Continued)

*Primary Examiner* — Julie Wu
*Assistant Examiner* — Carmencita M Belei
(74) *Attorney, Agent, or Firm* — Perkins Coie LLP; Viola T. Kung

(57) ABSTRACT

The present invention concerns the field of diagnostic biological markers. Specifically the invention relates to anti-BAG3 antibodies for use as biological markers for the diagnosis of a pathological state. Furthermore, the invention involves specific ELISA methods and kits, for detecting and evaluating, anti-BAG3 antibodies or BAG3/antibody complexes in a biological sample.

2 Claims, 28 Drawing Sheets

Specification includes a Sequence Listing.

(56) References Cited

OTHER PUBLICATIONS

Xu C, et al. "Apoptotic gene expression by human periodontal ligament cells following cyclic stretch." Journal of Periodontal Research. Dec. 2011; vol. 46(6); pp. 742-748.

Young P, et al. "Epstein-Barr virus nuclear antigen (EBNA) 3A induces the expression of and interacts with a subset of chaperones and co-chaperones." Journal of General Virology. Apr. 2008; vol. 89(Pt 4); pp. 866-877.

Jin X, et al. "Delineation of apoptotic genes for synergistic apoptosis of lexatumumab and anthracyclines in human renal cell carcinoma cells by polymerase chain reaction array." Anticancer Drugs. Apr. 2012; vol. 23(4); pp. 445-454.

De Marco M, et al. "BAG3 protein is induced during cardiomyoblast differentiation and modulates myogenin expression." Cell Cycle. Mar. 1, 2011; vol. 10(5); pp. 850-852.

International Search Report for International Application No. PCT/EP2013/061976, dated Jul. 18, 2013.

European Search Report for European Application No. 12172531.1, dated Jan. 25, 2013.

Wang, et al., "Expression of Bag family of heat shock protein in callus of healing mice", Journal of Yangzhou University (Agricultural and Life Science Edition), vol. 33 No. 1, Mar. 2012, pp. 6-9 (With English Abstract).

Falco et al., "BAG3 is a novel serum biomarker for pancreatic adenocarcinomas", American Journal of Gastroenterology, vol. 108, Jul. 2013, pp. 1178-1180.

Rosati et al., "Short Communications—Expression of the Antiapoptotic Protein BAG3 Is a Feature of Pancreatic Adenocarcinoma and Its Overexpression Is Associated With Poorer Survival", The American Journal of Pathology, vol. 181, Issue 5,, Nov. 2012, pp. 1524-1529.

Liao et al., FEBS Letter, vol. 503, pp. 151-157, 2001.

Bustin et al., J. Biomol. Tech. vol. 15, No. 3, pp. 155-166, 2004.

Zong et al. Genes Dev. vol. 15, No. 12, pp. 1481-1486, 2001.

Bussemakers MJG, et al. "DD3: A New Prostate-specific Gene, Highly Overexpressed in Prostate Cancer." Cancer Research. Dec. 1, 1999; 59(23); pp. 5975-5979.

Du ZX; et al. "Caspase-dependent cleavage of BAG3 in proteasome inhibitors-induced apoptosis in thyroid cancer cells." Biochemical and Biophysical Research Communications. May 9, 2008;369(3); pp. 894-898.

International Search Report for International Application No. PCT/EP2013/061971, dated Oct. 28, 2013.

Chen HY, et al. "Bag3 Gene Expression in Chronic Lymphocytic Leukemia and Its Association with Patients' Prognosis." Journal of Experimental Hematology I Chinese Association of Pathophysiology Aug. 2010; vol. 18(4 ); pp. 838-842.(English Abstract Only).

Feldman, et al., "BAG3 regulates contractility and Ca2+ homeostasis in adult mouse ventricular myocytes", Journal of Molecular and Cellular Cardiology. vol. 92, Jan. 19, 2016, pp. 10-20.

Final Office Action in U.S. Appl. No. 14/572,445, dated Jun. 23, 2017.

Jensen, "Real-Time Reverse Transcription Polymerase Chain Reaction to Measure mRNA: Use, Limitations, and Presentation of Results", The Anatomical Record, vol. 295, published online Nov. 2011, pp. 1-3.

Staibano et al., "BAG3 protein delocalisation in prostate carcinoma", Tumor Biology, vol. 31, Issue 5, Oct. 2010, pp. 461-469.

Thronton et al., "Real-time PCR (qPCR) primer design using free online software", Biochemistry and Molecular biology education, vol. 39, Issue 2, Mar. 28, 2011, pp. 145-154.

Zhang et al., "Bag3 promotes resistance to apoptosis through Bcl-2 family members in non-small cell lung cancer", Oncology Reports; vol. 27, Jan. 2012, pp. 109-113.

Homma, S. et al., BAG3 Deficiency Results in Fulminant Myopathy and Early Lethality, The American Journal of Pathology, 2006, vol. 169, No. 3, pp. 761-773.

Rosati A, et al. "BAG3: a multifaceted protein that regulates major cell pathways." Cell Death and Disease. Apr. 7, 2011;2:e141.

* cited by examiner

Figure 1D

| Pept:BAG3 aa | MW |
|---|---|
| 81-106 | 2937.56 |
| 107-121 | 1819.92 |
| 140-149 | 1102.51 |
| 231-249 | 2311.12 |
| 494-536 | 4621.39 |
| 538-575 | 3747.66 |

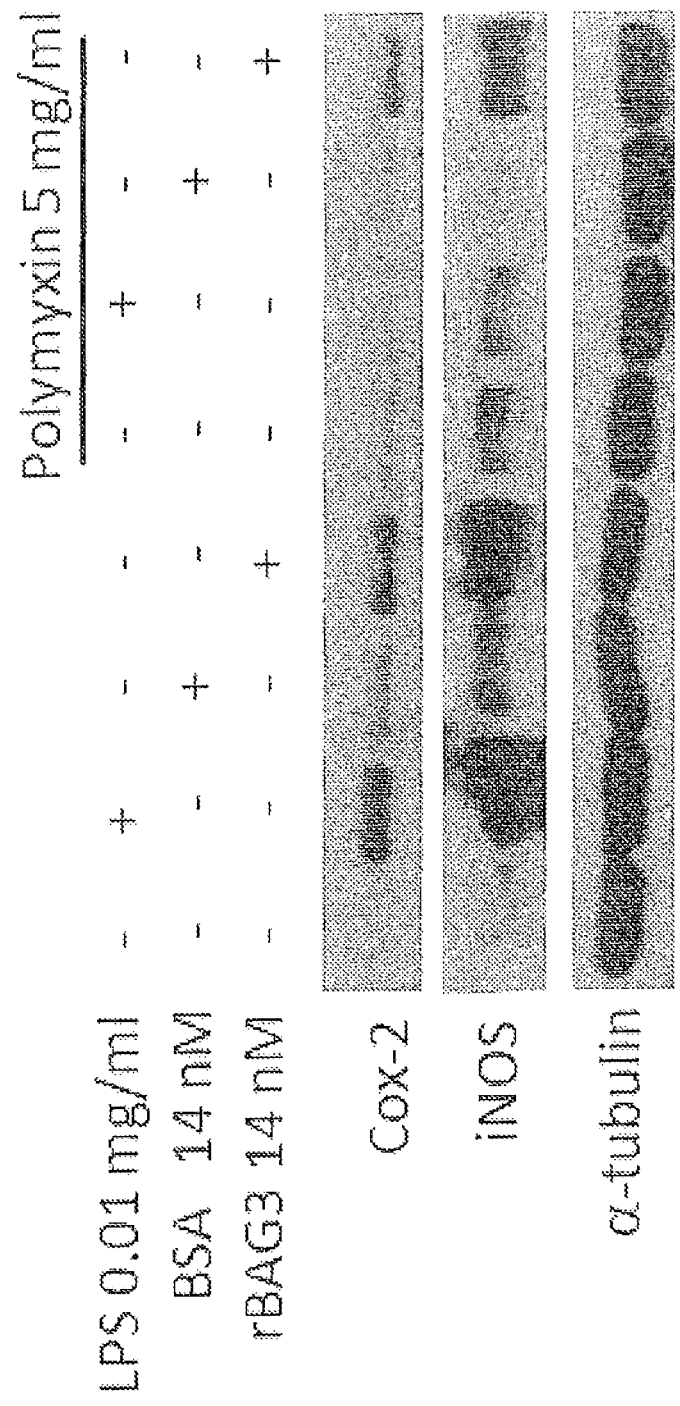
Figure 3C panel a

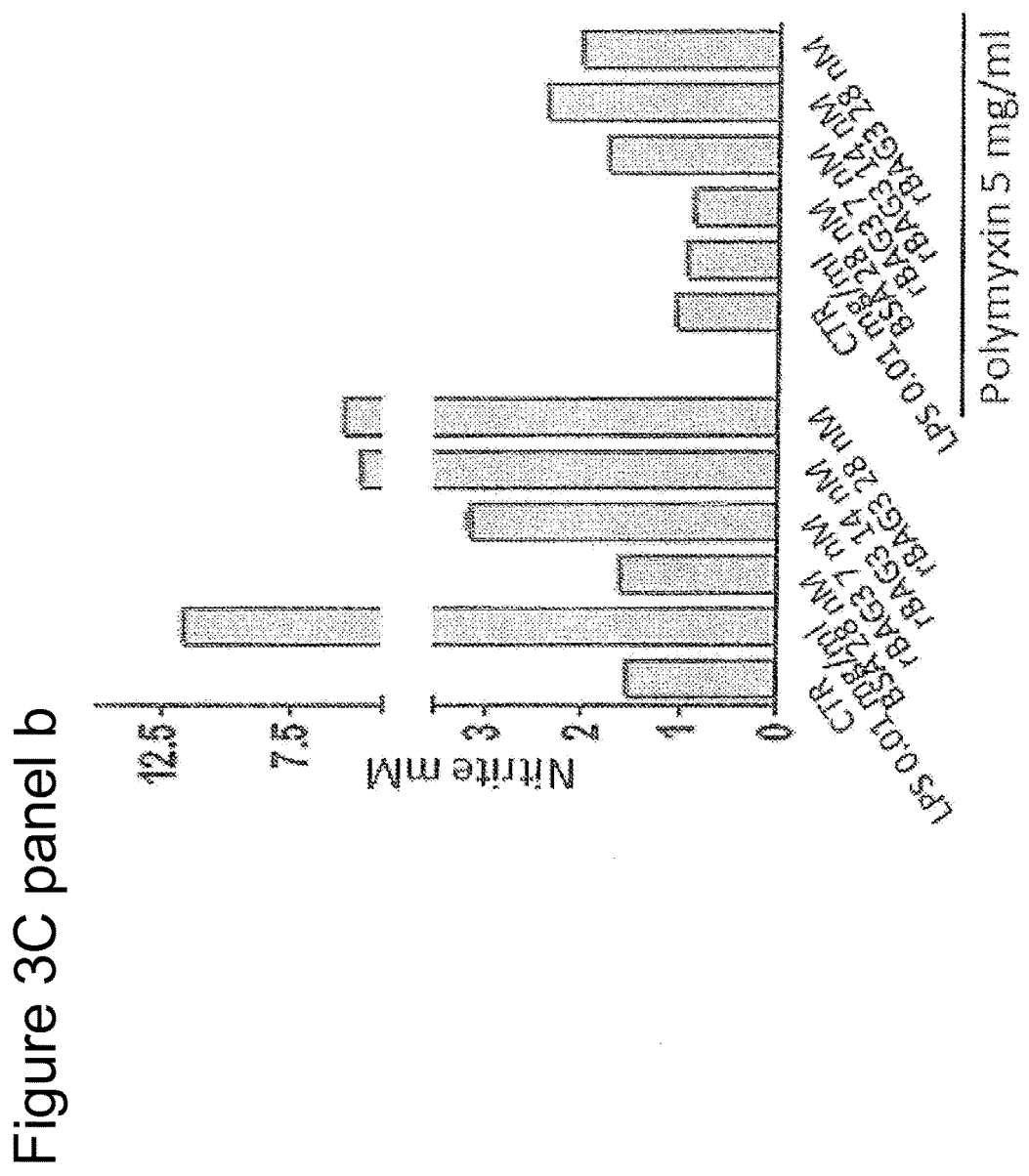
Figure 3C panel b

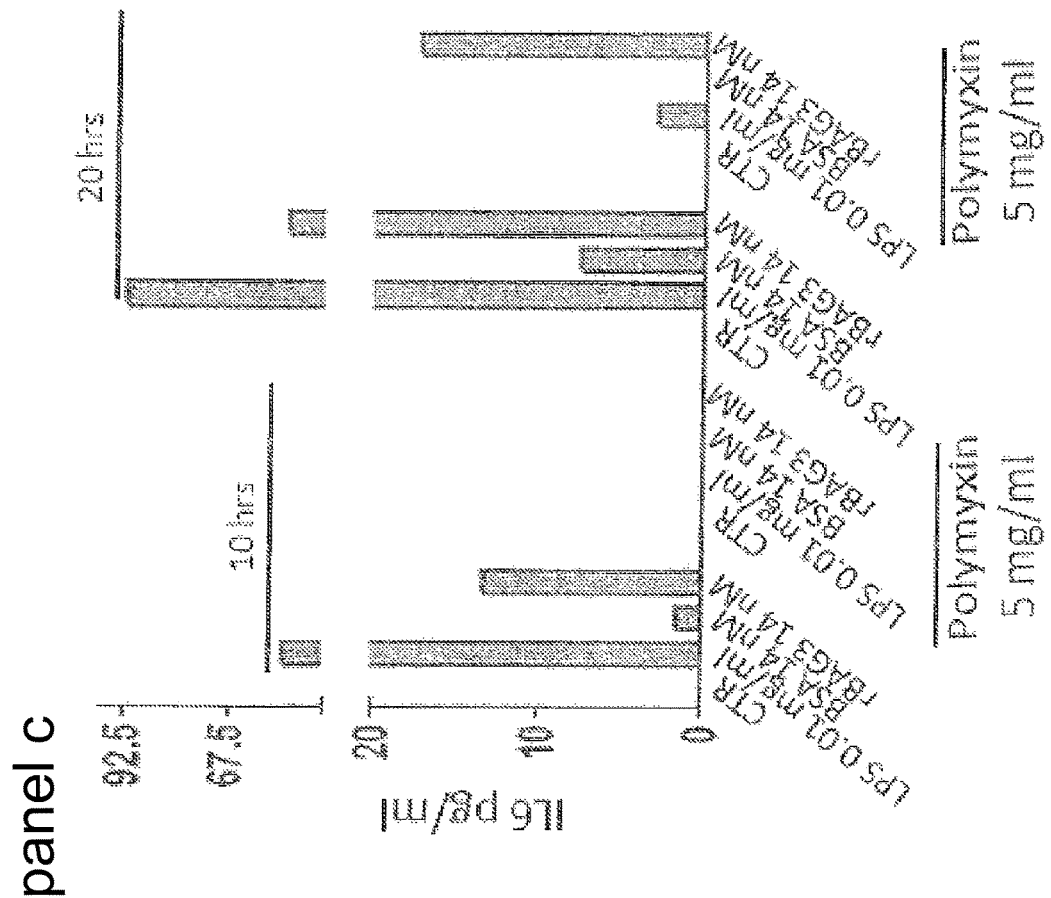
Figure 3C panel c

Figure 8E

SEQUENCE LISTING

<160> NUMBER OF SEQ ID NOS: 17

<210> SEQ ID NO 1
<211> LENGTH: 20
<212> TYPE: DNA
<213> ORGANISM: Homo sapiens
<220> FEATURE:
<221> NAME/KEY: source
<222> LOCATION: 1..20
<223> OTHER INFORMATION: /mol_type="unassigned DNA"
      /note="Forward primer"
      /organism="Homo sapiens"

<400> SEQUENCE: 1
aacggtgacc gcgacccttt                                          20

<210> SEQ ID NO 2
<211> LENGTH: 20
<212> TYPE: DNA
<213> ORGANISM: Homo sapiens
<220> FEATURE:
<221> NAME/KEY: source
<222> LOCATION: 1..20
<223> OTHER INFORMATION: /mol_type="unassigned DNA"
      /note="Reverse primer"
      /organism="Homo sapiens"

<400> SEQUENCE: 2
ccttccctag caggcggcag                                          20

<210> SEQ ID NO 3
<211> LENGTH: 20
<212> TYPE: DNA
<213> ORGANISM: Homo sapiens
<220> FEATURE:
<221> NAME/KEY: source
<222> LOCATION: 1..20
<223> OTHER INFORMATION: /mol_type="unassigned DNA"
      /note="Forward primer"
      /organism="Homo sapiens"

<400> SEQUENCE: 3
ccggctggcc cttcttcgtg                                          20

<210> SEQ ID NO 4
<211> LENGTH: 20
<212> TYPE: DNA
<213> ORGANISM: Homo sapiens
<220> FEATURE:
<221> NAME/KEY: source
<222> LOCATION: 1..20
<223> OTHER INFORMATION: /mol_type="unassigned DNA"
      /note="Reverse primer"
      /organism="Homo sapiens"

<400> SEQUENCE: 4
cagcctagag ccctcccggg                                          20

<210> SEQ ID NO 5
<211> LENGTH: 20
<212> TYPE: DNA
<213> ORGANISM: Homo sapiens
<220> FEATURE:
<221> NAME/KEY: source
<222> LOCATION: 1..20
<223> OTHER INFORMATION: /mol_type="unassigned DNA"
      /note="Forward primer"
      /organism="Homo sapiens"

<400> SEQUENCE: 5

-continued gtcacctctg cggggcatgc                                                   20

<210> SEQ ID NO 6
<211> LENGTH: 20
<212> TYPE: DNA
<213> ORGANISM: Homo sapiens
<220> FEATURE:
<221> NAME/KEY: source
<222> LOCATION: 1..20
<223> OTHER INFORMATION: /mol_type="unassigned DNA"
      /note="Reverse primer"
      /organism="Homo sapiens"

<400> SEQUENCE: 6
ggtgactgcc caggctgctc                                                   20

<210> SEQ ID NO 7
<211> LENGTH: 20
<212> TYPE: DNA
<213> ORGANISM: Homo sapiens
<220> FEATURE:
<221> NAME/KEY: source
<222> LOCATION: 1..20
<223> OTHER INFORMATION: /mol_type="unassigned DNA"
      /note="Forward primer"
      /organism="Homo sapiens"

<400> SEQUENCE: 7
ccagcctccc acggacctga                                                   20

<210> SEQ ID NO 8
<211> LENGTH: 20
<212> TYPE: DNA
<213> ORGANISM: Homo sapiens
<220> FEATURE:
<221> NAME/KEY: source
<222> LOCATION: 1..20
<223> OTHER INFORMATION: /mol_type="unassigned DNA"
      /note="Reverse primer"
      /organism="Homo sapiens"

<400> SEQUENCE: 8
ctggtgactg cccaggctgc                                                   20

<210> SEQ ID NO 9
<211> LENGTH: 20
<212> TYPE: DNA
<213> ORGANISM: Homo sapiens
<220> FEATURE:
<221> NAME/KEY: source
<222> LOCATION: 1..20
<223> OTHER INFORMATION: /mol_type="unassigned DNA"
      /note="Forward primer"
      /organism="Homo sapiens"

<400> SEQUENCE: 9
caggagcagc acgccactcc                                                   20

<210> SEQ ID NO 10
<211> LENGTH: 20
<212> TYPE: DNA
<213> ORGANISM: Homo sapiens
<220> FEATURE:
<221> NAME/KEY: source
<222> LOCATION: 1..20
<223> OTHER INFORMATION: /mol_type="unassigned DNA"
      /note="Reverse primer"
      /organism="Homo sapiens"

```
<400> SEQUENCE: 10
tggtccaact gggcctggct                                               20

<210> SEQ ID NO 11
<211> LENGTH: 16
<212> TYPE: PRT
<213> ORGANISM: Homo sapiens
<220> FEATURE:
<223> OTHER INFORMATION: protein

<400> SEQUENCE: 11

Asp Arg Asp Pro Leu Pro Pro Gly Trp Glu Ile Lys Ile Asp Pro Gln
1               5                   10                  15

<210> SEQ ID NO 12
<211> LENGTH: 15
<212> TYPE: PRT
<213> ORGANISM: Homo sapiens
<220> FEATURE:
<223> OTHER INFORMATION: Protein

<400> SEQUENCE: 12

Ser Ser Pro Lys Ser Val Ala Thr Glu Glu Arg Ala Ala Pro Ser
1               5                   10                  15

<210> SEQ ID NO 13
<211> LENGTH: 15
<212> TYPE: PRT
<213> ORGANISM: Homo sapiens
<220> FEATURE:
<223> OTHER INFORMATION: Protein

<400> SEQUENCE: 13

Asp Lys Gly Lys Lys Asn Ala Gly Asn Ala Glu Asp Pro His Thr
1               5                   10                  15

<210> SEQ ID NO 14
<211> LENGTH: 15
<212> TYPE: PRT
<213> ORGANISM: Homo sapiens
<220> FEATURE:
<223> OTHER INFORMATION: Protein

<400> SEQUENCE: 14

Asn Pro Ser Ser Met Thr Asp Thr Pro Gly Asn Pro Ala Ala Pro
1               5                   10                  15

<210> SEQ ID NO 15
<211> LENGTH: 575
<212> TYPE: PRT
<213> ORGANISM: Homo sapiens
<220> FEATURE:
<223> OTHER INFORMATION: BAG-3

<400> SEQUENCE: 15

Met Ser Ala Ala Thr His Ser Pro Met Met Gln Val Ala Ser Gly Asn
1               5                   10                  15

Gly Asp Arg Asp Pro Leu Pro Pro Gly Trp Glu Ile Lys Ile Asp Pro
                20                  25                  30

Gln Thr Gly Trp Pro Phe Phe Val Asp His Asn Ser Arg Thr Thr Thr
            35                  40                  45

Trp Asn Asp Pro Arg Val Pro Ser Glu Gly Pro Lys Glu Thr Pro Ser
        50                  55                  60

Ser Ala Asn Gly Pro Ser Arg Glu Gly Ser Arg Leu Pro Pro Ala Arg
```

```
            65                  70                  75                  80
Glu Gly His Pro Val Tyr Pro Gln Leu Arg Pro Gly Tyr Ile Pro Ile
                    85                  90                  95

Pro Val Leu His Glu Gly Ala Glu Asn Arg Gln Val His Pro Phe His
                100                 105                 110

Val Tyr Pro Gln Pro Gly Met Gln Arg Phe Arg Thr Glu Ala Ala Ala
                115                 120                 125

Ala Ala Pro Gln Arg Ser Gln Ser Pro Leu Arg Gly Met Pro Glu Thr
            130                 135                 140

Thr Gln Pro Asp Lys Gln Cys Gly Gln Val Ala Ala Ala Ala Ala Ala
145                 150                 155                 160

Gln Pro Pro Ala Ser His Gly Pro Glu Arg Ser Gln Ser Pro Ala Ala
                165                 170                 175

Ser Asp Cys Ser Ser Ser Ser Ser Ala Ser Leu Pro Ser Ser Gly
                180                 185                 190

Arg Ser Ser Leu Gly Ser His Gln Leu Pro Arg Gly Tyr Ile Ser Ile
            195                 200                 205

Pro Val Ile His Glu Gln Asn Val Thr Arg Pro Ala Ala Gln Pro Ser
        210                 215                 220

Phe His Gln Ala Gln Lys Thr His Tyr Pro Ala Gln Gln Gly Glu Tyr
225                 230                 235                 240

Gln Thr His Gln Pro Val Tyr His Lys Ile Gln Gly Asp Asp Trp Glu
                245                 250                 255

Pro Arg Pro Leu Arg Ala Ala Ser Pro Phe Arg Ser Ser Val Gln Gly
                260                 265                 270

Ala Ser Ser Arg Glu Gly Ser Pro Ala Arg Ser Ser Thr Pro Leu His
            275                 280                 285

Ser Pro Ser Pro Ile Arg Val His Thr Val Val Asp Arg Pro Gln Gln
        290                 295                 300

Pro Met Thr His Arg Glu Thr Ala Pro Val Ser Gln Pro Glu Asn Lys
305                 310                 315                 320

Pro Glu Ser Lys Pro Gly Pro Val Gly Pro Glu Leu Pro Pro Gly His
                325                 330                 335

Ile Pro Ile Gln Val Ile Arg Lys Glu Val Asp Ser Lys Pro Val Ser
                340                 345                 350

Gln Lys Pro Pro Pro Ser Glu Lys Val Glu Val Lys Val Pro Pro
            355                 360                 365

Ala Pro Val Pro Cys Pro Pro Ser Pro Gly Pro Ser Ala Val Pro
        370                 375                 380

Ser Ser Pro Lys Ser Val Ala Thr Glu Glu Arg Ala Ala Pro Ser Thr
385                 390                 395                 400

Ala Pro Ala Glu Ala Thr Pro Pro Lys Pro Gly Glu Ala Glu Ala Pro
                405                 410                 415

Pro Lys His Pro Gly Val Leu Lys Val Glu Ala Ile Leu Glu Lys Val
                420                 425                 430

Gln Gly Leu Glu Gln Ala Val Asp Asn Phe Glu Gly Lys Lys Thr Asp
            435                 440                 445

Lys Lys Tyr Leu Met Ile Glu Glu Tyr Leu Thr Lys Glu Leu Leu Ala
450                 455                 460

Leu Asp Ser Val Asp Pro Glu Gly Arg Ala Asp Val Arg Gln Ala Arg
465                 470                 475                 480

Arg Asp Gly Val Arg Lys Val Gln Thr Ile Leu Glu Lys Leu Glu Gln
                485                 490                 495
```

```
Lys Ala Ile Asp Val Pro Gly Gln Val Gln Val Tyr Glu Leu Gln Pro
            500                 505                 510

Ser Asn Leu Glu Ala Asp Gln Pro Leu Gln Ala Ile Met Glu Met Gly
        515                 520                 525

Ala Val Ala Ala Asp Lys Gly Lys Lys Asn Ala Gly Asn Ala Glu Asp
    530                 535                 540

Pro His Thr Glu Thr Gln Gln Pro Glu Ala Thr Ala Ala Ala Thr Ser
545                 550                 555                 560

Asn Pro Ser Ser Met Thr Asp Thr Pro Gly Asn Pro Ala Ala Pro
                565                 570                 575

<210> SEQ ID NO 16
<211> LENGTH: 17
<212> TYPE: DNA
<213> ORGANISM: Homo sapiens
<220> FEATURE:
<221> NAME/KEY: source
<222> LOCATION: 1..17
<223> OTHER INFORMATION: /mol_type="unassigned DNA"
      /note="Forward primer"
      /organism="Homo sapiens"

<400> SEQUENCE: 16
cctgttagct gtggttg                                                    17

<210> SEQ ID NO 17
<211> LENGTH: 22
<212> TYPE: DNA
<213> ORGANISM: Homo sapiens
<220> FEATURE:
<221> NAME/KEY: source
<222> LOCATION: 1..22
<223> OTHER INFORMATION: /mol_type="unassigned DNA"
      /note="Reverse primer"
      /organism="Homo sapiens"

<400> SEQUENCE: 17
aacatacaga tattcctatg gc                                              22
```

BAG3 AS BIOCHEMICAL SERUM AND TISSUE MARKER

This application is a continuation of PCT/EP2013/061976, filed Jun. 11, 2013; which claims priority to European Application No. 12172531.1, filed Jun. 19, 2012. The contents of the above-identified applications are incorporated herein by reference in their entireties.

REFERENCE TO SEQUENCE LISTING, TABLE OR COMPUTER PROGRAM

The Sequence Listing is concurrently submitted herewith with the specification as an ASCII formatted text file via EFS-Web with a file name of Sequence_Listing.txt with a creation date of Dec. 15, 2014, and a size of 9.0 kilobytes. The Sequence Listing filed via EFS-Web is part of the specification and is hereby incorporated in its entirety by reference herein.

TECHNICAL FIELD

The present invention concerns anti-BAG3 antibodies for use as biochemical markers in the diagnosis of a pathological state.

STATE OF THE ART

BAG3 (RefSeq: NP_004272; Gene ID 9531) is a 74 kDa cytoplasmic protein particularly concentrated in the rough endoplasmic reticulum. BAG3 protein belongs to the family of co-chaperones that interact with the ATPase domain of the heat shock protein HSP70 through the structural domain known as BAG domain (110-124 amino acids). In addition to the BAG domain, BAG3 contains a WW domain and a proline-rich repeat (PXXP), that can mediate binding to other proteins. Furthermore, two conserved IPV (Ile-Pro-Val) motifs are located between the WW and the PXXP regions and mediate BAG3 binding to HspB8, a member of the HspB family of molecular chaperones. Therefore BAG3, due to the adaptor nature of its multidomain structure, can interact with different partner proteins. bag3 gene expression is constitutive in a few normal cell types, including myocytes, and in several primary tumours or tumour cell lines. Moreover it can be induced by a variety of stressors: indeed stressful stimuli activate the heat shock transcription factor (HSF) 1, that is responsible for the expression of stress-activated genes, including bag3 (Rosati A, Graziano V, De Laurenzi V, Pascale M, Turco M C. BAG3: a multifaceted protein that regulates major cell pathways. Cell Death Dis. 2011; 2: e141). Evidence indicates that BAG3 has a role in sustaining cell survival, by modulating, in either Hsp70-dependent or -independent fashion, the levels or localisation of apoptosis-regulating proteins, such as IKKγ, Bax or BRAF, depending on cell context.

BAG3 protein appears to be expressed during cardiomyoblasts differentiation and to sustain myogenin expression. These findings indicate an involvement of BAG3 in late heart development (De Marco M, Turco M C, Rosati A. BAG3 protein is induced during cardiomyoblast differentiation and modulates myogenin expression. Cell Cycle. 2011; 10: 850-852). Moreover, in cardiomyocytes BAG3 has been shown to localize at Z-disc and interact with the actin capping protein, CapZβ1, stabilizing myofibril structure and possibly preserving myofibrillar integrity during mechanical stress. BAG3 mutations can impair the Z-disc assembly and increase the sensitivity to stress-induced apoptosis. In keeping with the role of BAG3 in the survival and myofibrillar integrity in cardiocytes and, in general, in muscle cells, mutations in bag3 gene have been associated with some forms of myofibrillar myopathy and dilated cardiomyopathy.

Up to now both a cytoplasmic BAG3 and soluble serical form of BAG3 have been detected and found associated with different pathologies, as well as more generally to cell survival.

The need and importance is increasingly felt for the identification of a biological marker which allows the rapid identification of such pathologies, without having the disadvantages of being associated with invasive diagnostics in a surprisingly specific and sensitive manner, and/or that can allow to early detect the pathology, monitor the effect of therapy, predict the risk of complication, perform an informative follow-up.

SUMMARY OF THE INVENTION

The present invention concerns anti-BAG3 antibodies for use as biochemical markers in the diagnosis of a pathological state. Preferably said anti-BAG3 antibodies are bound to soluble BAG3 to form immune complexes.

According to a preferred embodiment of the present invention said diagnosis is in vitro or ex vivo.

A further aspect of the present invention is that the recipient of said diagnosis is a mammalian, preferably a human.

As will be further described in the detailed description of the invention, the use of the anti-BAG-3 antibodies of the present invention has the advantages of being specific for a pathological state selected from the group consisting of a heart disease, cancer, diabetes, inflammation and inflammatory related diseases of the skin, nerves, bones, blood vessels and connective tissues.

According to an embodiment of the invention, said heart disease is selected from: angina pectoris, pre-infarction angina, myocardial infarction, heart failure, ischemia, acute coronary disease, acute heart failure, chronic heart failure and iatrogenic heart disease.

According to another embodiment of the invention, said cancer is selected from: pancreatic cancer, bladder cancer and prostate cancer.

A further embodiment of the present invention is a method for detecting the presence of an anti-BAG3 antibody or an anti-BAG3 antibody bound to soluble BAG3 to form an immune complex in a biological sample, comprising the steps of:

a. obtaining a biological sample, consisting of serum, plasma, urine or saliva,
b. determining the presence of anti-BAG3 or BAG3 associated antibodies in the biological sample.

According to a preferred embodiment, the method of the present invention further comprises the additional step of:

c. comparing the values obtained from biological sample with reference values or with the values obtained from healthy donors.

In a preferred embodiment, said determination step b. is performed by an ELISA test.

According to a preferred embodiment of the present invention said serum, plasma, urine or saliva is from a mammalian, preferably a human.

According to a preferred embodiment in the method of the present invention the presence of said anti-BAG3 antibody or said immune complex is associated with a pathological condition.

Preferably, said pathological condition is selected from the group consisting of a heart disease, cancer, diabetes, inflammation and inflammatory related diseases of the skin, nerves, bones, blood vessels and connective tissues.

Preferably said heart disease is selected from: angina pectoris, pre-infarction angina, myocardial infarction, heart failure, ischemia, acute coronary disease, acute heart failure, chronic heart failure and iatrogenic heart disease.

According to a preferred embodiment of the present invention said cancer is selected from: pancreatic cancer, bladder cancer and prostate cancer.

A further embodiment of the present invention is an ELISA kit, comprising a BAG3 recombinant protein or BAG3-specific mouse monoclonal antibodies AC-1, AC-2 AC-3, AC-4, AC-5, AC-rb1a, AC-rb1b, AC-rb2a, AC-rb2b, AC-rb3a, AC-rb3b, AC-rb4a and AC-rb4b for capturing soluble BAG3 and antibodies able to recognize human immunoglobulins, as well as its use for the detection of anti-BAG3 antibodies or anti-BAG3 antibodies bound to soluble BAG3 to form an immune complexes in a biological sample.

Preferably said biological sample is a serum, plasma, urine or saliva sample.

In a preferred embodiment of the present invention said serum, plasma, urine or saliva sample is from a mammalian, preferably a human.

The invention still further relates to a immunohistochemistry (IHC) kit for the detection of BAG3 protein in a biological sample, wherein said biological sample is preferably a tissue sample, comprising BAG3-specific antibodies and reagents including probes needed for the staining.

BRIEF DESCRIPTION OF THE DRAWINGS

FIG. 1D: Bands obtained in two patients affected by chronic heart failure were excised from the gel and its identity analyzed by mass spectrometry using the program MASCOT.

FIG. 3C panel a—Analysis of Cox-2 and iNOS levels in J774 A1 macrophages incubated with BAG3. J774 A1 cells at 80% confluency were incubated with control medium, BSA, LPS or rBAG3, for 20 hours. Polymixin was added where indicated to verify that the effects of E. coli-derived rBAG3 were independent from the presence of contaminating endotoxin. Cox-2 and iNOS expression were analyzed in cell lysates by Western blotting.

FIG. 3C panel b—Analysis of nitrite release from J774 A1 macrophages incubated with BAG3. J774 A1 cells at 80% confluency were incubated with control medium, BSA, LPS or rBAG3 for 24 hours. 100 µl of supernatants from each sample were incubated with 100 µl of Griess reagent; the optical density at 550 nm (OD550) was measured with a Beckman DU62 spectrophotometer. Nitrite concentration was evaluated by comparing the OD550 of the sample with that of a standard curve of sodium nitrite.

FIG. 3C panel c—Analysis of IL-6 release from J774 A1 macrophages incubated with BAG3. J774 A1 cells at 80% confluency macrophages were incubated with control medium, BSA, LPS or recombinant BAG3 for 5 hours. BAG3 peptides (peptide 1, peptide 2, peptide 3, peptide 4 or scrambled peptide) 625 nM were added where indicated to verify their ability to block BAG3 activity. IL-6 production was measured in cell culture medium using an ELISA test. IL-6 concentration was evaluated by comparing the OD of the sample with that of a standard curve of recombinant IL-6.

Representative images of BAG3 staining using the monoclonal anti-BAG3 antibody AC-1 in normal pancreas tissue. Sections were counterstained with hematoxylin. Staining revealed a moderate positivity of Langerhans islets, while normal pancreatic ducts and pancreatic acinar cells had no BAG3 expression.

FIG. 4B:

Representative images of BAG3 low positive and BAG3 high positive tumor samples stained using a monoclonal anti-BAG3 antibody revealed with a biotinylated secondary antibody. Sections were counterstained with hematoxylin. Two different magnifications are shown: 100× (left panels) and 400× (right panels). We assigned a score based on the proportion of positive cancer cells in the sample by counting the number of positive cells over the total cancer cells in 10 non-overlapping fields using a 400× magnification. The median percentage of BAG3 positive cells, calculated as described, was 40% and this value was used as a cut-off to separate low and high positive samples.

FIG. 4C:

Survival curves were made comparing 39 patients with low BAG3 staining (≤40% of positive cells) and 27 patients with high BAG3 staining (>40% of positive cells). All patients analyzed underwent R0 resection of the pancreatic adenocarcinoma. Median survival increases from 12 months in the high positive group to 23 months in the low positive group. Log-rank test p-value=0.0013.

Figure 5:
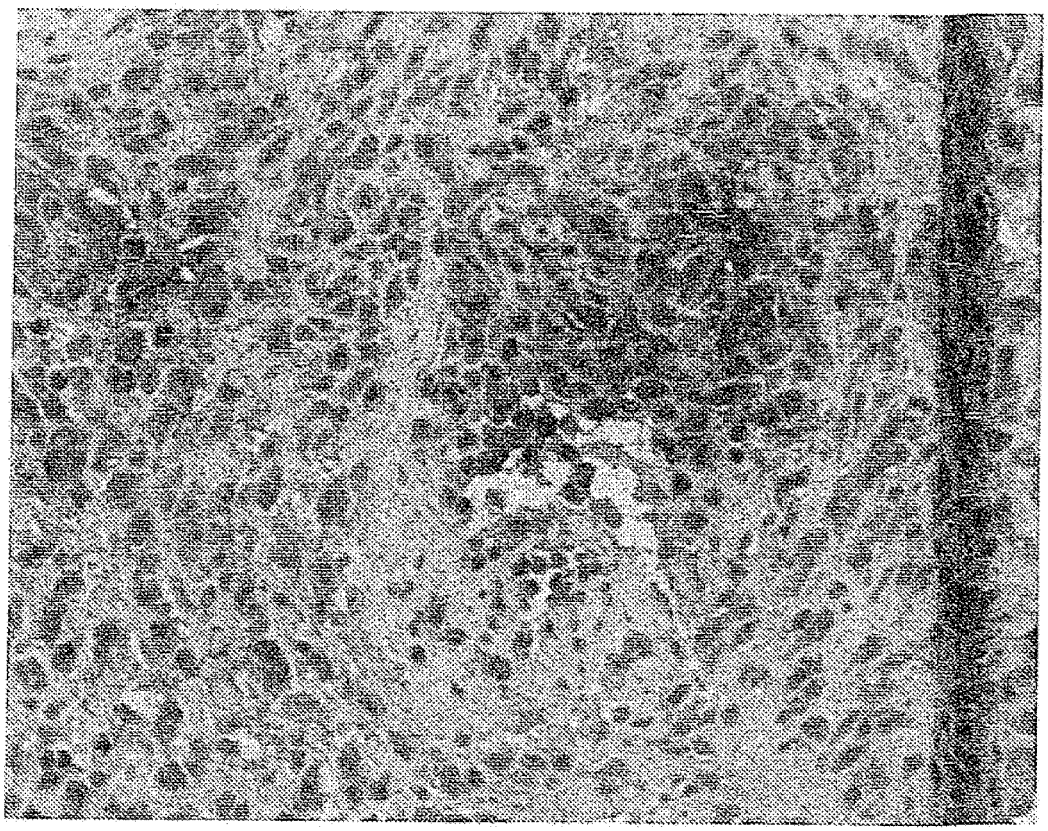

FIG. 5: Representative image of BAG3 staining in synovial tissues from several rheumatoid arthritis. BAG3 positivity is observed in synovial fibroblasts and inflammatory infiltrates. Sections were counterstained with hematoxylin.

Figure 6:
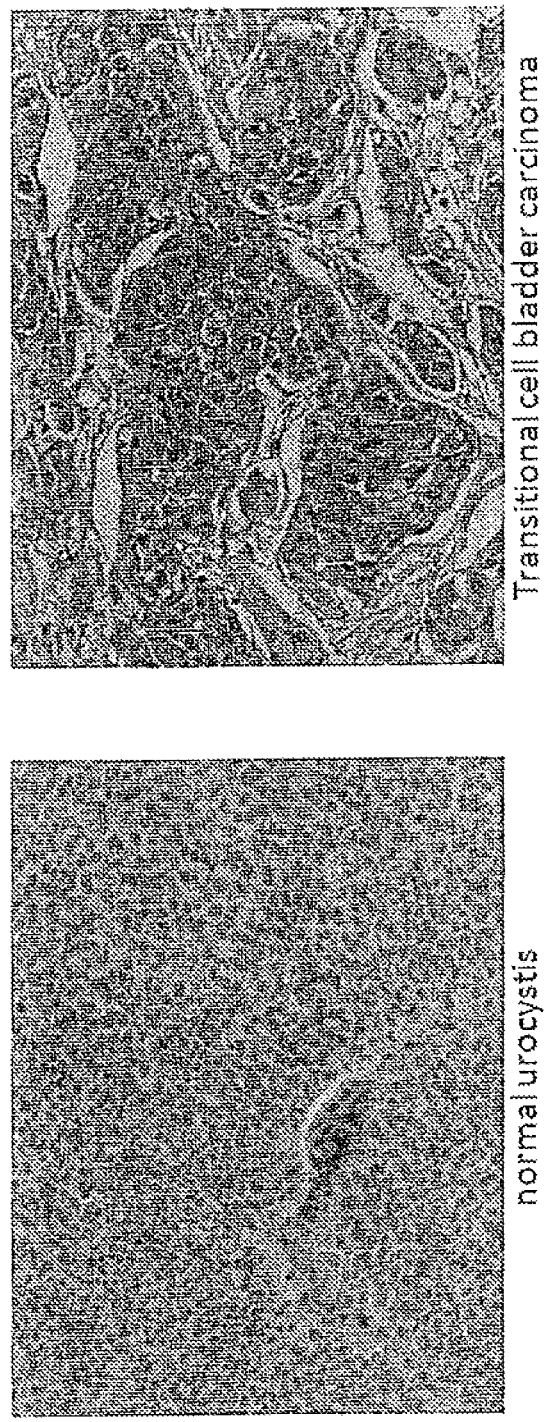

FIG. 6: Representative image of BAG3 staining in normal urocystis that resulted negative and in transitional cell bladder carcinoma that resulted highly positive for BAG3 in cytoplasm of tumor cells. Sections were counterstained with hematoxylin.

FIG. 7A:

bag3 mRNA relative expression evaluated by qRT-PCR is shown in a graph where values are reported as mean+S.D. The blue line represents the median value calculated.

FIG. 7B:

Survival analysis was made for all patients analyzed with qRT-PCR. 13 patients with high bag3 expression had shorter survival (median survival=19.0 months) as compared to 12 patients with low bag3 expression (median survival=32.0 months). Log-rank test p-value=0.0198.

FIG. 8A:

Pancreatic cancer cell lines (PSN1, Capan-1, AsPC-1, PANC-1 and MIA PaCa-2) were treated with different concentrations of gemcitabine as indicated in the graph. After 48 hours, apoptotic cell death was analyzed. Graph depicts mean percentage of Sub G0/G1 cells (±S.D.). Data are representative of three independent experiments.

FIG. 8B:

Western blot analysis of BAG3 in pancreatic cancer cell lines; GAPDH housekeeping protein contents were used to monitor equal loading conditions.

FIG. 8C:

MIA PaCa-2 and PANC-1 cell lines were treated with 2 µM gemcitabine (GEM) for the indicated times BAG3 protein expression levels were monitored by western blot.

FIG. 8D:

bag3 mRNA levels were analyzed by RT-PCR; graph depicts relative bag3 mRNA levels (±S.D.) and data are representative of three indipendent experiments.

FIG. 8E:

MIA PaCa-2 and PANC-1 cell lines were transfected with BAG3 siRNA or a non-targeted siRNA (NTsiRNA) for 72 hours and then treated with 2 µM gemcitabine (GEM) for 24 h. BAG3 levels were analyzed by western blot and GAPDH levels were detected to monitor equal loading conditions.

FIG. 8F:

MIA PaCa-2 and PANC-1 cells were transfected as described above and treated with 2 aM gemcitabine (GEM) for 24 h or 48 h. Apoptotic cell death was analyzed as described. Graph depicts mean percentage of Sub G0/G1 cells (±S.D.). Data are representative of three independent experiments.

Figure 9A:
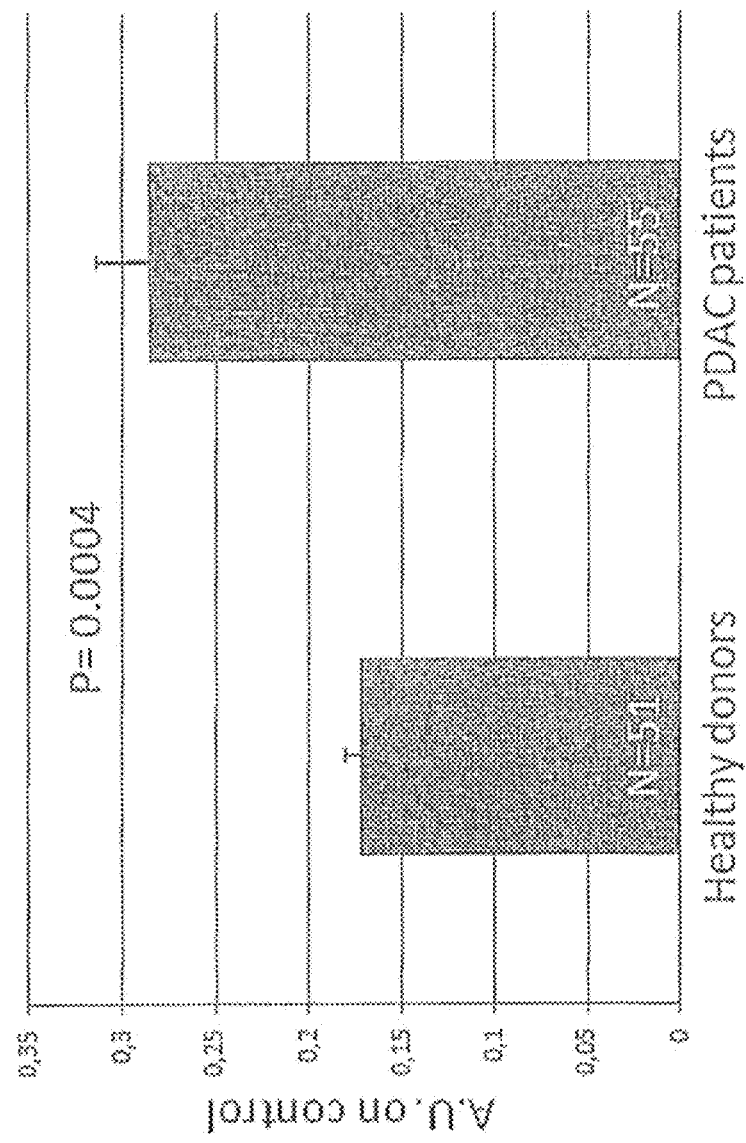

FIG. 9A: Detection of BAG3 specific immuno-complexes by ELISA test. Sera from 55 pancreatic adenocarcinoma patients were compared with sera from 51 healthy donors for the presence of BAG3 specific immune-complexes in a specific ELISA test. Results are plotted as arbitrary units+S.E.

Figure 9B:
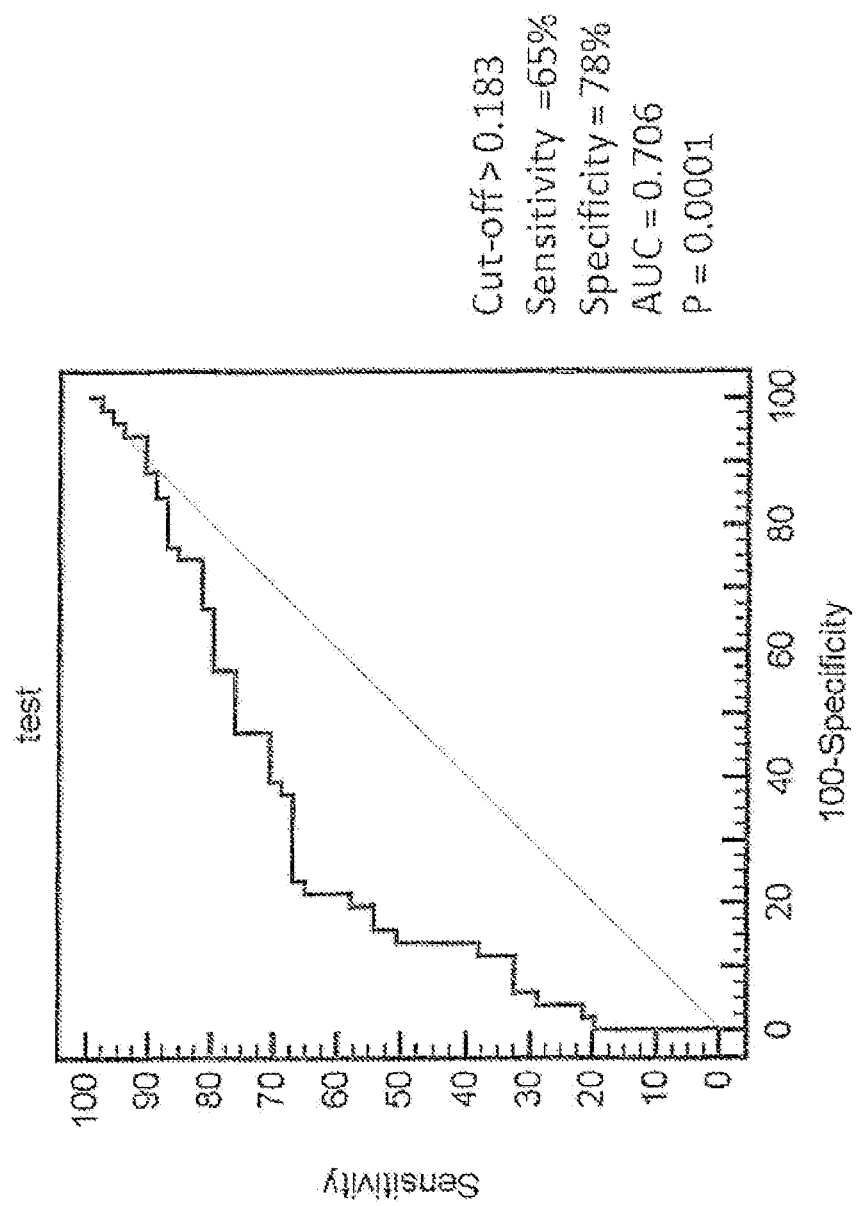

FIG. 9B: ROC analysis of ELISA test results. Cut-off on 0.183 A.U. results in 65% sensitivity and 78% specificity.

Figure 10:
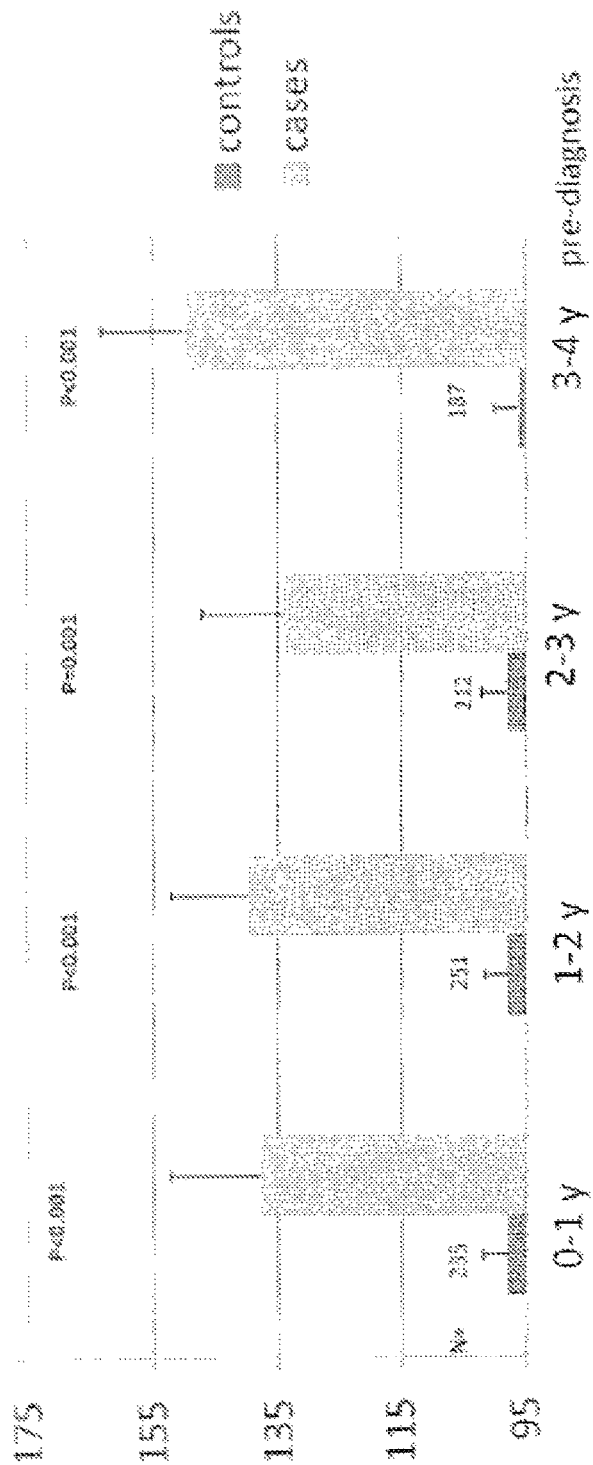

FIG. 10: Detection of BAG3-specific antibodies in patients sera from 49 female subjects at 0-1 years pre-diagnosis for pancreatic adenocarcinoma were compared with sera from 235 female control subjects sera for the presence of BAG3 specific antibodies in a specific ELISA test. Control sera were about five for each case subjects and age matched with the respective case. Others time points included: 53 subjects at 1-2 years pre-diagnosis for PDAC compared to 251 controls; 44 subjects at 2-3 years pre-diagnosis for PDAC compared to 212 controls; 42 subjects at 3-4 years pre-diagnosis for PDAC compared to 187 controls.

Results are plotted as arbitrary units±S. P value was calculated with student's t test.

DETAILED DESCRIPTION OF THE INVENTION

The present invention concerns anti-BAG3 antibodies for use as biochemical markers in the diagnosis of a pathological state.

With the term "diagnosis" in the present invention we refer to medical diagnosis (often simply termed diagnosis) that refers to the process of attempting to determine or identify a possible disease or disorder. The diagnosis of the present invention encompasses also the early diagnosis With the term "early diagnosis" we refer to the capacity of the test to discriminate a pathological state before specific or aspecific symptoms.

Anti-BAG3 antibodies have now been advantageously detected in serum, plasma, urine or saliva. Until now such antibodies had never been found in serum either in physiological or pathological condition. The detection of anti-BAG3 antibodies in serum has the advantage of being a rapid and non-invasive technique be exploited for diagnostic, early diagnosis and prognostic purposes, risk stratification, as a tool for the identification and for monitoring therapies.

A further advantage of the detection of antibodies is that a very small amount of serum is required for the detection. In fact, soluble BAG3 protein can also be detected in the serum of patients suffering from some pathologies, but the amount of serum requested for the detection of the soluble protein is much higher than that required for the detection of antibodies. Furthermore, it is possible that soluble BAG3 protein levels can be much lower than those of antibodies and/or that, respect to soluble BAG3 protein, antibodies can be detectable in earlier phases of specific pathologies and/or can more efficiently predict risk of complications or monitor the effects of therapies.

A further embodiment of the present invention is that said anti-BAG3 antibodies can be advantageously detected in different biological samples selected from serum, plasma, urine or saliva.

In the present invention, by serum is intended the component of blood that is neither a blood cell nor a clotting factor; it is the blood plasma with the fibrinogens removed. Serum includes all proteins not used in blood clotting (coagulation) and all the electrolytes, antibodies, antigens, hormones, and any exogenous substances.

In the present invention, by plasma is intended the straw-coloured/pale-yellow liquid component of blood that normally holds the blood cells in whole blood in suspension. It contains clotting factors, such as fibrinogens.

In a further embodiment, the invention provides the use of anti-BAG3 antibodies as biochemical markers, wherein said anti-BAG3 antibodies are bound to soluble BAG3 to form immune complexes.

Anti-BAG3 antibodies, either free or bound to soluble BAG3 to form immune complexes have advantageously been now detected in a biological sample, and may be used as a marker in the diagnosis of a pathological condition. The detection of such antibodies and/or immune complexes in a biological sample also has the advantage of being a rapid and non-invasive technique for diagnostic and/or prognostic purposes.

According to a preferred embodiment of the present invention said diagnosis is in vivo or ex vivo.

A further embodiment of the present invention is that recipient of said diagnosis is a mammalian, preferably a human.

In the present invention, by immune complex or protein/antibody complex is intended the integral binding of an antibody to a soluble antigen, the bound antigen acting as a specific epitope, bound to an antibody is referred to as a singular immune complex.

Such immune complexes have the same advantages seen as for the detection of antibodies, since a very small amount of serum is required also for the detection of the immune complex. The amount of serum required for the detection of soluble BAG3 is much higher also than that required for the detection of the protein/antibody (immune) complexes. Immune complexes as well as free antibodies can be detectable in earlier phases of specific pathologies and can more efficiently predict risk of complications or monitor the effects of therapies.

A still further embodiment of the invention is the use of anti-BAG3 antibodies or said immune complexes (formed by anti-BAG3 antibodies bound to soluble BAG3) as biological markers of a pathological state, wherein said pathological state is a heart disease, cancer, diabetes, inflammation and inflammatory related diseases of the skin, nerves, bones, blood vessels and connective tissues.

Preferably said heart disease is selected from the group consisting of: angina pectoris, pre-infarction angina, ischemia, myocardial infarction, heart failure, acute coronary disease, acute heart failure, chronic heart failure and iatrogenic heart disease.

According to a preferred embodiment of the present invention said cancer is selected from: pancreatic cancer, bladder cancer and prostate cancer.

A further embodiment of the present invention is a method for detecting the presence of an anti-BAG3 antibody or an anti-BAG3 antibody bound to soluble BAG3 to form an immune complex in a biological sample, comprising the steps of:
  a. obtaining a biological sample, consisting of serum, plasma, urine or saliva,
  b. determining the presence of anti-BAG3 or BAG3 associated antibodies in the biological sample.

The method according to the present invention has the advantage of allowing to detect significant differences between anti-BAG3 antibodies and/or BAG3/antibodies complexes between healthy individuals and patients affected by BAG3-involving pathologies. The proposed assay method allows a statistically significant separation of the group of cardiac patients from the group of healthy people. It can also stratify such patients with heart disease in subgroups of patients at increased risk (heart failure, HF).

In a still further aspect the invention relates to a method for detecting the presence of an anti-BAG3 antibody in a biological sample or an anti-BAG3 antibody bound to soluble BAG3 to form an immune complex, further comprising the step of:
  c. comparing the values obtained from the biological sample with reference values or with the values obtained from healthy donors.

In a preferred aspect the method according to the present invention is a method wherein said determination step b. is performed by an ELISA test.

According to a preferred embodiment in the method of the present invention said serum, plasma, urine or saliva is from a mammalian, preferably a human.

The method according to the present invention has the advantage of allowing the rapid and non-invasive detection of the biological markers allowing the evaluation of pathologies, risks for diseases and/or their complications, and monitoring of therapies.

According to a further aspect the invention relates to a detection method wherein the presence of said anti-BAG3 antibody or said anti-BAG3 antibody bound to soluble BAG3 to form an immune complex is associated with a pathological condition.

In a preferred embodiment said pathological condition is chosen from the group consisting of heart disease, cancer, diabetes, inflammation and inflammatory related diseases of the skin, nerves, bones, blood vessels and connective tissues.

In particular said heart disease is selected from the group consisting of: angina pectoris, pre-infarction angina, myocardial infarction, ischemia, heart failure, acute coronary disease, acute heart failure, chronic heart failure or iatrogenic heart disease.

According to a preferred embodiment of the present invention said cancer is selected from: pancreatic cancer, bladder cancer and prostate cancer.

The invention further relates to an ELISA kit for the detection of anti-BAG3 antibodies or anti-BAG3 antibodies bound to soluble BAG3 to form an immune complexes in a biological sample.

The ELISA kit according to the present invention comprises a BAG3 recombinant protein for capturing anti-BAG3 antibodies or BAG3-specific mouse monoclonal antibodies AC-1, AC-2, AC-3, AC-4, AC-5, AC-rb1a, AC-rb1b, AC-rb2a, AC-rb2b, AC-rb3a, AC-rb3b, AC-rb4a and AC-rb4b, for capturing soluble BAG3 and antibodies able to recognize human immunoglobulins.

Such antibodies can be enzyme-linked antibodies able to recognize human immunoglobulins.

The invention also relates to a kit for the detection of BAG3-associated antibodies in a biological sample and is performed by ELISA with BAG3-specific mouse monoclonal antibodies AC-1, AC-2, AC-3, AC-4, AC-5, AC-rb1a, AC-rb1b, AC-rb2a, AC-rb2b, AC-rb3a, AC-rb3b, AC-rb4 and AC-rb4b, for capturing soluble BAG3 and enzyme-linked antibodies for the detection able to recognize human immunoglobulins.

Preferably said biological sample is a serum, plasma, urine or saliva sample.

In a preferred embodiment of the present invention said serum, plasma, urine or saliva sample is from a mammalian, preferably a human.

The invention still further relates to a immunohistochemistry (IHC) kit for the detection of BAG3 protein in a biological sample, wherein said biological sample is preferably a tissue sample. Tissue samples can be biopsies, frozen tissues, paraffin embedded tissues.

The IHC kit according to the present invention comprises BAG3-specific antibodies and reagents including probes needed for the staining.

Said BAG3-specific antibodies can be mouse monoclonal antibodies AC-1, AC-2 and AC-3 and/or enzyme-linked antibodies for the detection able to recognize mouse immunoglobulins.

In particular, the IHC kit advantageously allows to reveal BAG3 protein in 100% of pancreatic carcinoma tissue samples from patients that undergo pancreas resection and is expressed in most bladder carcinoma samples. Furthermore, BAG3 protein can be revealed with the kit for BAG3 detection by IHC also in normal pancreas tissue in Langerhans islets while other normal tissues result negative (such for example normal urocystis). BAG3 positivity can be also observed in synovial fibroblasts and inflammatory infiltrates in rheumatoid arthritis tissue samples.

Long-term survival of patients affected by PDAC is very poor: only about 4% of patients will live 5 years after diagnosis. Indeed, surgical reception is presently the only chance of cure, but only approximately 20% of patients are diagnosed with resectable disease; furthermore, in a large proportion (about 80%) of such subset of patients the metastatization process is already occurring at diagnosis, and indeed distant metastases appear after surgical resection. Hence we need to better understand early stages in the development of pancreatic cancer and identify molecules that can allow detecting them. Also, markers that can allow a better prognosis and help the choice of therapies are highly required.

Advantageously the BAG3 IHC kit allows the identification of the prognosis of PDAC patients. It was seen that the intensity of BAG3 expression identified by IHC, correlates with patients' survival. Therefore it can be used for both prognosis and for making a choice of therapy.

A still further aspect of the invention is a kit for the detection of BAG3 gene expression in a biological sample comprising a set of amplification primers. Preferably said amplification primers are suitable for the detection by quantitative real-time RT-PCR.

Specific primers bag3 primers according to primer sets 1 to 5, which are described below and identified by the SEQ ID NO. 1 to SEQ ID NO. 10, allow the detection and quantification of BAG3 expression by quantitative real-time PCR.

```
Primer set 1
fw: SEQ ID NO. 1:
AACGGTGACCGCGACCCTTT;

rev: SEQ ID NO. 2:
CCTTCCCTAGCAGGCGGCAG

Primer set 2
fw: SEQ ID NO. 3:
CCGGCTGGCCCTTCTTCGTG;

rev: SEQ ID NO. 4:
CAGCCTAGAGCCCTCCCGGG
```

```
-continued
Primer set 3
fw: SEQ ID NO. 5:
GTCACCTCTGCGGGGCATGC;

rev: SEQ ID NO. 6:
GGTGACTGCCCAGGCTGCTC

Primer set 4
fw: SEQ ID NO. 7:
CCAGCCTCCCACGGACCTGA;

rev: SEQ ID NO. 8:
CTGGTGACTGCCCAGGCTGC

Primer set 5
fw: SEQ ID NO. 9:
CAGGAGCAGCACGCCACTCC;

rev: SEQ ID NO. 10:
TGGTCCAACTGGGCCTGGCT.
```

The RT-PCR kit for bag3 mRNA detection in a biological sample allows to correlate the levels of bag3 gene expression with patients' survival and can be used for prognosis and for choice of therapy. Preferably said biological sample is a tissue sample.

A still further aspect of the invention is represented by anti-BAG3 monoclonal antibodies, their fragments, and peptides corresponding to specific aminoacidic sequences of BAG3 protein that are able to block macrophage activation and can therefore be used for therapy of inflammatory, oncologic or other diseases involving macrophage activation. See in particular FIG. 3 and Table I.

This invention relates to the use of BAG3-specific mouse monoclonal antibodies AC-1, AC-2 and AC-3 or same modified as F(ab), F(ab')2, F(ab) or humanized; or peptides comprising sequences as follows:

```
PEP 1:
                                          (SEQ ID NO. 11)
DRDPLPPGWEIKIDPQ

PEP2:
                                          (SEQ ID NO. 12)
SSPKSVATEERAAPS

PEP3:
                                          (SEQ ID NO. 13)
DKGKKNAGNAEDPHT

PEP4:
                                          (SEQ ID NO. 14)
NPSSMTDTPGNPAAP
``` as molecules able to bind and/or block soluble BAG3 effects.

EXAMPLES

Example 1

Serum Deprivation-Induced Stress in Cultured Human Primary Cardiomyocytes and the Rat Cardiomyocyte Cell Line H9c2

Figure 1A:
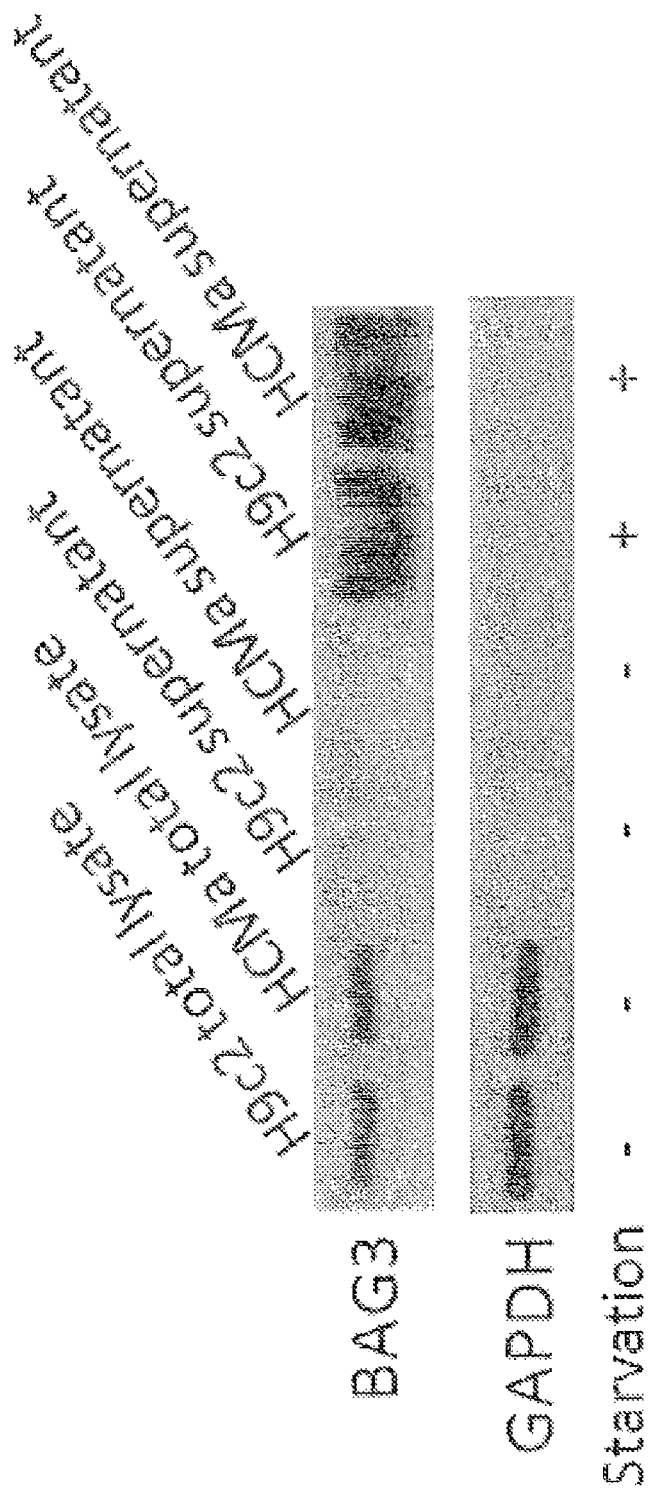
FIG. 1A: detection of BAG3 protein in supernatants from cultured cardiomyocytes. Human (HCMa) and rat (H9c2) cardiomyocytes at 80% confluency were incubated with or without 10% FBS for 16 hours at 37° C. in a 5% $CO_2$ atmosphere. Supernatants were dialyzed in a buffer containing 50 mM NaCl and 0.05% IGEPAL, lyophilized, resuspended in 1 ml of RIPA buffer (50 mM Tris HCl pH 7.6, 150 mM sodium chloride, 2 mM sodium orthovanadate, 4 mM EDTA, 10 mM sodium pyrophosphate, 1% NP-40, 0.1% sodium deoxycholate), and analyzed with anti-BAG3 or anti-GAPDH antibodies by western blotting.
Figure 1B:
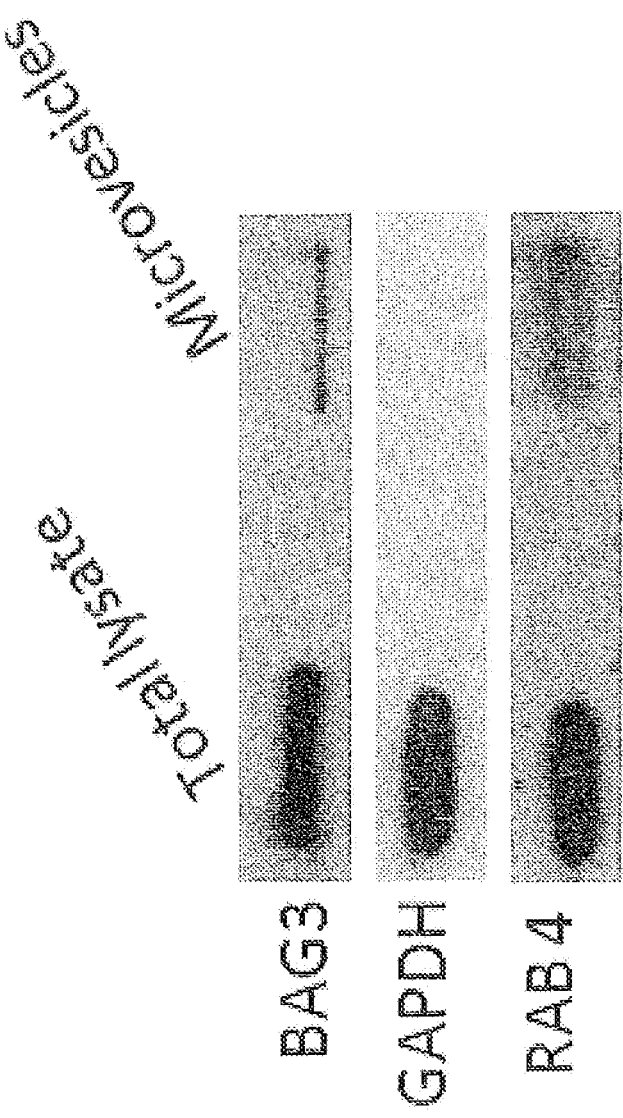
FIG. 1B: detection of BAG3 protein in exocytic vesicles. Surnatants obtained from H9c2 cells were subjected to sequential centrifugations: (i) 2'000×g for 15 min, to remove cells; (ii) 10'000×g for 30 min, to remove cellular debris; (iii) 150'000×g for 90 min, to pellet exocytic vesicles. The pellet was washed once in PBS at 150'000×g for 90 min and analyzed with the anti-BAG3 TOS-2 polyclonal antibody in comparison with a whole-cell lysate by western blot. Rab-4 was analyzed as a marker for exocytic vesicles. GAPDH, a cytosolic protein, was analyzed as a control.

Cardiomyocytes are known to release protective factors in mounting a response against stressful agents. Since stress-induced proteins, such as Hsp70, Hp27, Hsp90 and others, although exerting an intracellular activity, can also be secreted in response to stress, BAG3 release by cardiomyocytes was analyzed in stressful conditions. For this purpose, we analyzed the effect of serum deprivation-induced stress in cultured human primary cardiomyocytes or the rat cardiomyocyte cell line H9c2. As shown in FIG. 1, we could detect BAG3 protein in the supernatants of cardiomyocytes exposed to serum deprivation for 16 h (FIG. 1A). Since at that time point cell survival was not affected by serum deprivation (results not shown), we discarded the hypothesis that BAG3 release was due to cell necrosis. Therefore we verified whether BAG3 was present in exocytic vesicles. Indeed, by isolating extracellular vesicles through a differential centrifugation procedure (16), we found that they contained BAG3 protein (FIG. 1B).

Figure 1C:
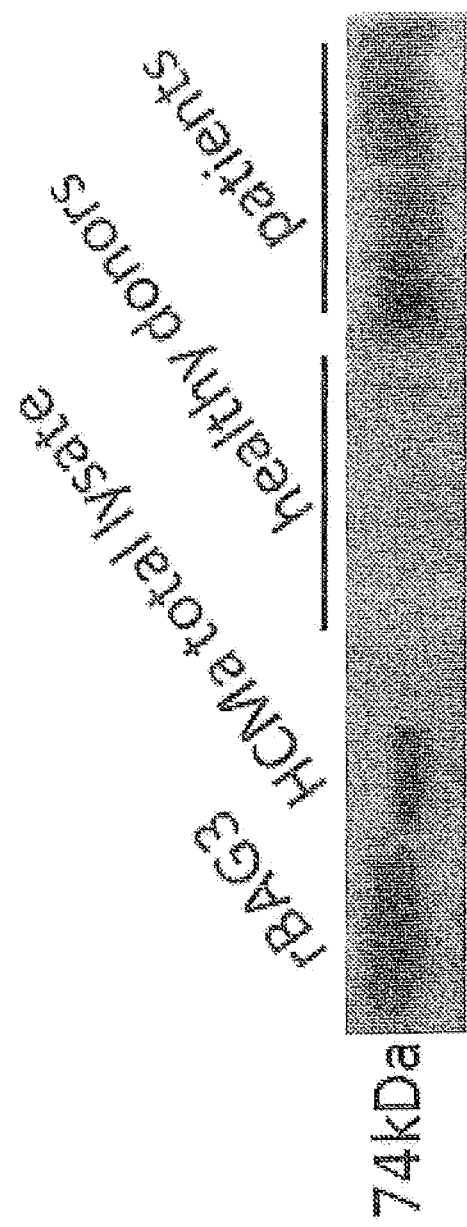
FIG. 1C: Sera from two healthy donors and from two patients affected by chronic heart failure were analyzed with the anti-BAG3 antibody TOS-2 polyclonal antibody in western blotting.

To further verify the existence of a soluble form of BAG3, we investigated its presence in two blood sera from patients affected by chronic heart failure (CHF). Through western blot analysis, we could identify a band recognized by anti-BAG3 antibody. We excised the band and subjected it to mass spectrometry, confirming its identity (FIG. 1C). This evidence confirmed that the protein could be detected in an extracellular form. We could not detect the protein in sera from healthy donors (FIG. 1C).

Peptides recognized and matched by mass spectrometry on the entire BAG3 protein sequence are indicated in bold:

```
                                               (SEQ ID NO: 15)
MSAATHSPMM QVASGNGDRD PLPPGWEIKI DPQTGWPFFV

DHNSRTTTWN DPRVPSEGPK ETPSSANGPS REGSRLPPAR

EGHPVYPQLR PGYIPIPVLH EGAENRQVHP FHVYPQPGMQ

RFRTEAAAAA PQRSQSPLRG MPETTQPDKQ CGQVAAAAAA

QPPASHGPER SQSPAASDCS SSSSSASLPS SGRSSLGSHQ

LPRGYISIPV IHEQNVTRPA AQPSFHQAQK THYPAQQGEY

QTHQPVYHKI QGDDWEPRPL RAASPFRSSV QGASSREGSP

ARSSTPLHSP SPIRVHTVVD RPQQPMTHRE TAPVSQPENK

PESKPGPVGP ELPPGHIPIQ VIRKEVDSKP VSQKPPPPSE

KVEVKVPPAP VPCPPPSPGP SAVPSSPKSV ATEERAAPST

APAEATPPKP GEAEAPPKHP GVLKVEAILE KVQGLEQAVD

NFEGKKTDKK YLMIEEYLTK ELLALDSVDP EGRADVRQAR

RDGVRKVQTI LEKLEQKAID VPGQVQVYEL QPSNLEADQP

LQAIMEMGAV AADKGKKNAG NAEDPHTETQ QPEATAAATS

NPSSMTDTPG NPAAP.
```

The human BAG 3 protein has the amino acid sequence according to SEQ ID NO:15.

Example 2

Anti-BAG3 Antibodies in CHF Patients' Sera

Figure 2A:
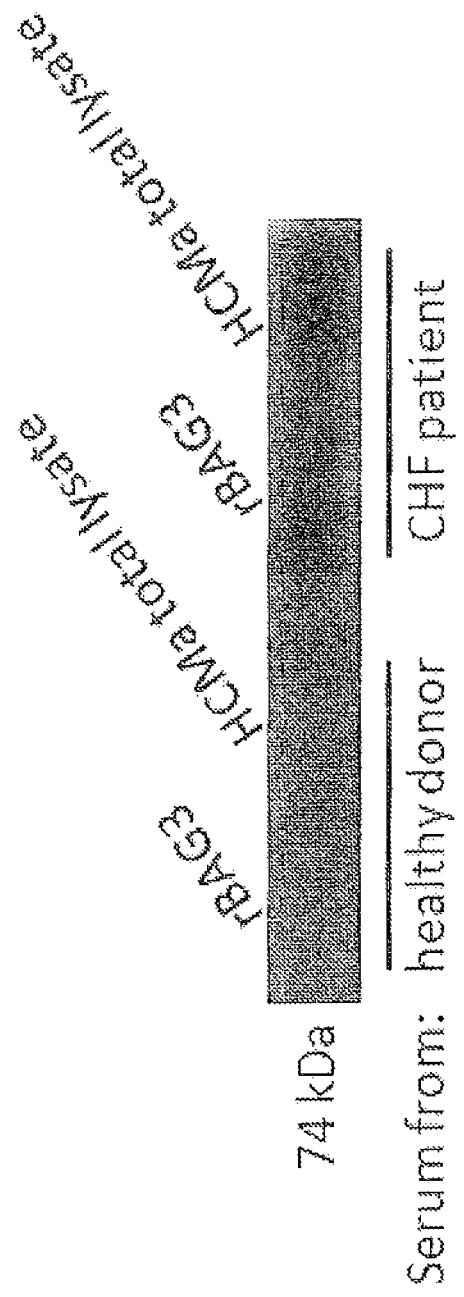
FIG. 2A: detection of BAG3 protein in sera from CHF patients. BAG3 recombinant protein and whole-cell lysate from HCMa cells were analyzed by western blotting with serum (1:40) obtained from a patient with heart failure. Analysis with serum from a healthy donor was performed as negative control.
Figure 2B:
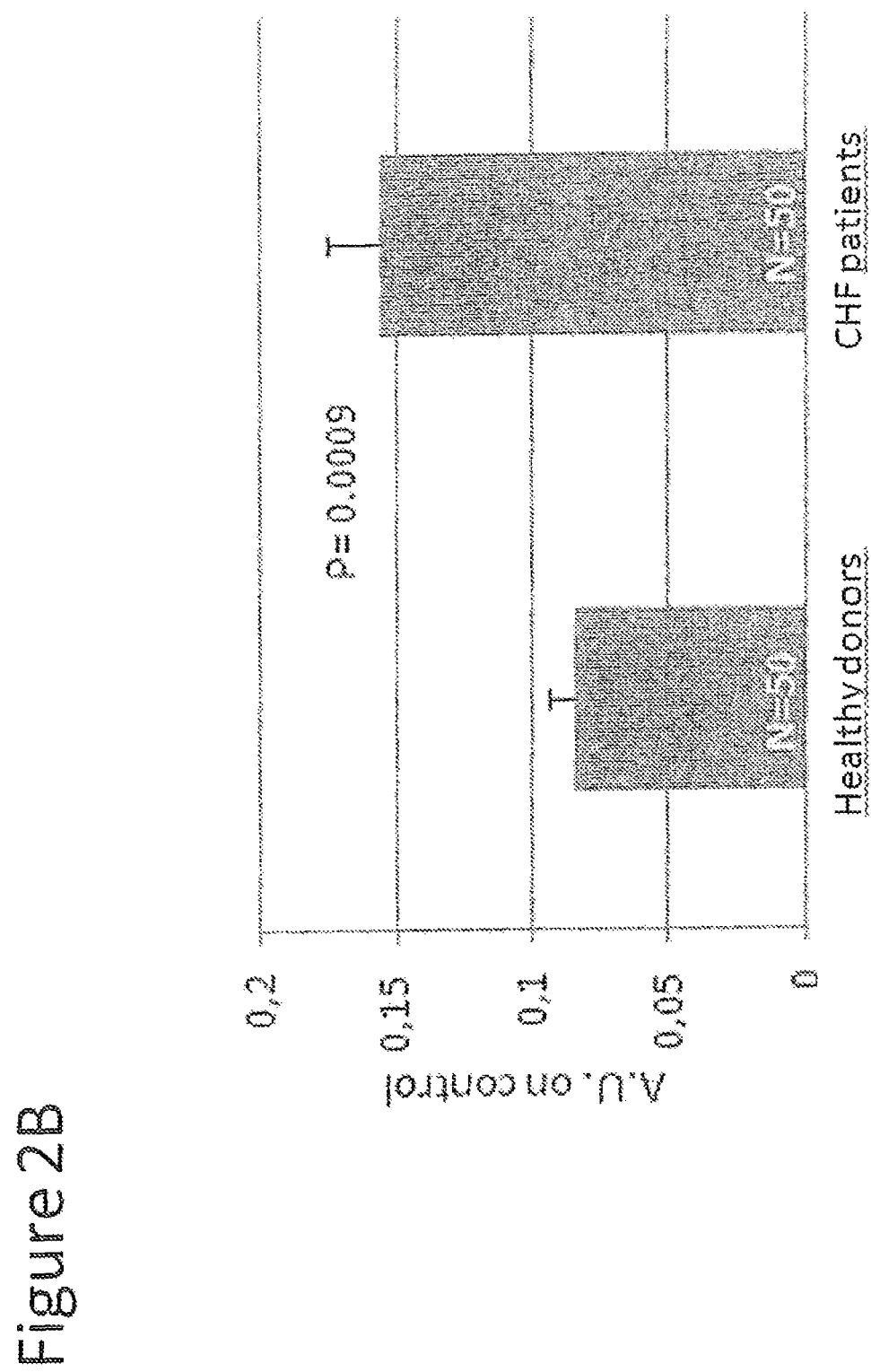
FIG. 2B: detection of anti-BAG3 antibodies by ELISA test. Sera from 50 CHF patients (with ejection fraction<60%) were compared with sera from 50 healthy donor for the presence of anti-BAG3 antibodies in a specific ELISA test. Results are plotted as arbitrary units.
Figure 2C:
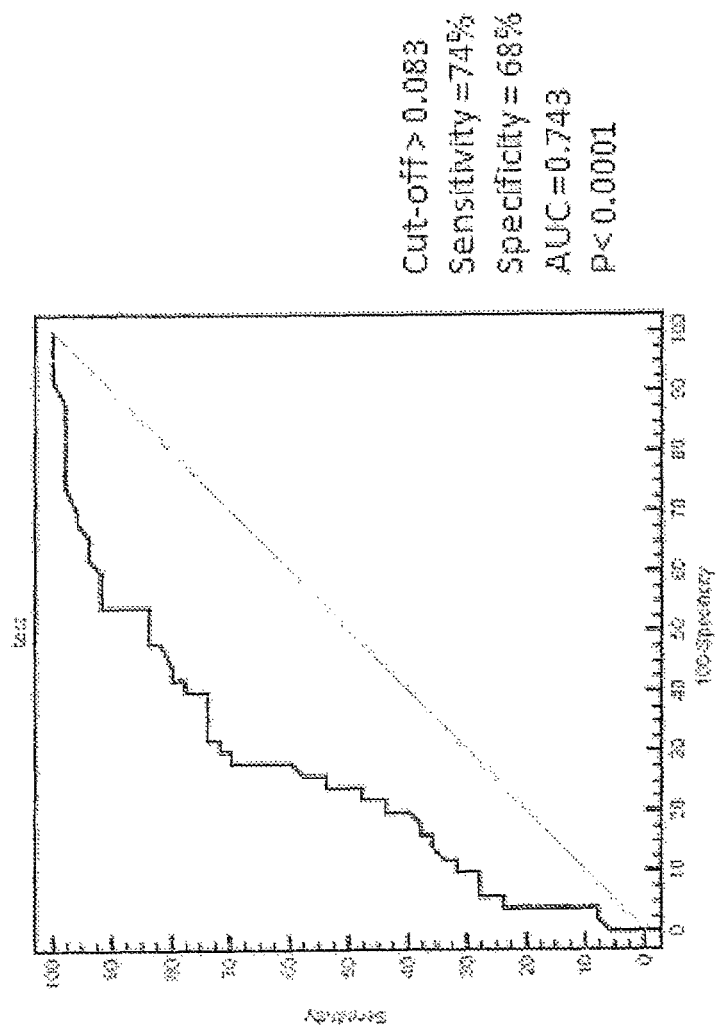
FIG. 2C: ROC analysis of ELISA test results. Cut-off on 0.083 A.U. results in 74% sensitivity and 68% specificity.

We found that sera from CHF patients recognized BAG3 protein in western blotting, using an anti-human IgG as secondary antibody (results representative of experiments with sera from three different patients are shown in FIG. 2A). This result indicated the presence of anti-BAG3 antibodies in CHF patients' sera. To confirm this finding, we analyzed sera from 50 CHF patients (with ejection fraction<60%) compared with sera from 50 healthy donors, for the presence of anti-BAG3 antibodies in a specific ELISA test. As shown in FIG. 2B, we detected significantly higher values of anti-BAG3 antibodies in patients' compared to controls' sera. ROC analysis of ELISA test results, using as cut-off 0.083 A.U., in 74% sensitivity and 68% specificity (FIG. 2C).

Example 3

BAG3 Binding to Macrophages

Figure 3A:
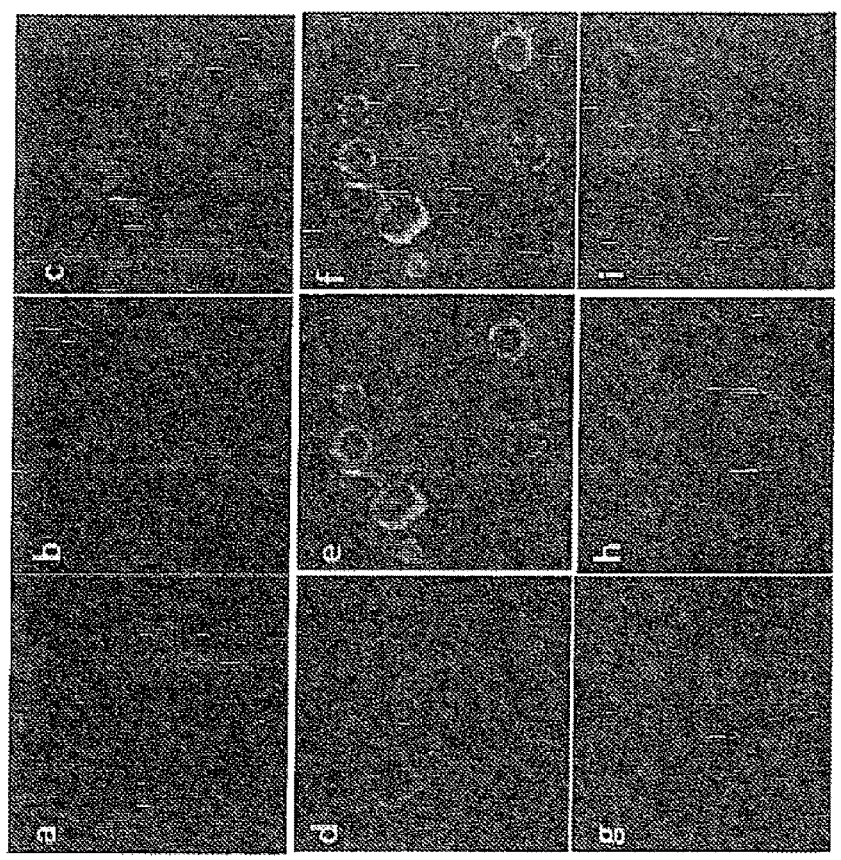
FIG. 3A: Confocal microscopy analysis of direct fluorescence performed for detection of rBAG3-FITC binding to HCMa cells (a, b, c) and J774 A1 cells (d, e, f, g, h, i). BAG3 recombinant protein and purified BSA (albumin from bovine serum purchased from SIGMA) were conjugated to FITC using the FluoroTag FITC Conjugation Kit purchased from SIGMA following the manufacturer instructions. Equal amount of rBAG3-FITC (b, e) and BSA-FITC (h) proteins, calculated following the manufacturer instructions, were added in HCM and J774 A1 culture media with 0.1% NaN3 for β-integrin was analyzed as control (a, d, g). Cells were analyzed by a Zeiss LSM confocal microscope. Merged images are shown in c, f and i.
Figure 3B:
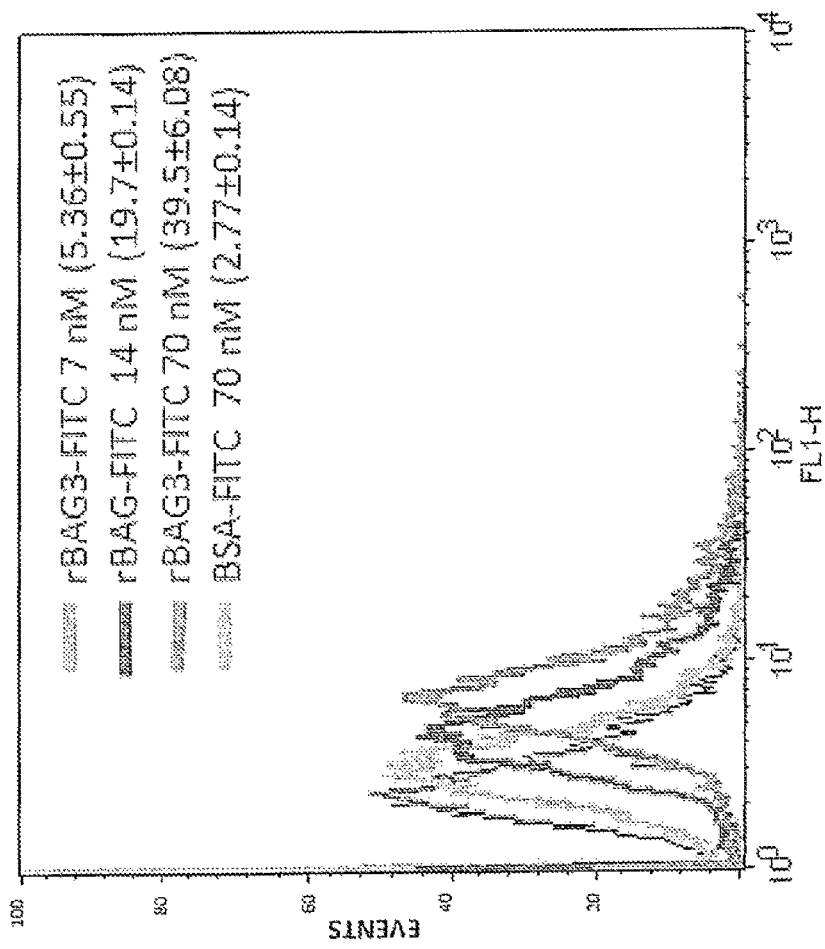
FIG. 3B: BAG3 binds macrophages. J774 A1 macrophages ($1 \times 10^6$ cells/ml) were incubated with different concentration of Fitc-BAG3 protein (7, 14 and 70 nm). FITC-BSA (70 nM) was used as a negative control (grey). Cells fluorescence was analyzed by flow cytometry.

We addressed the functional significance of BAG3 release by cardiomyocytes. We excluded that the protein could be involved in an autocrine pathway, because it did not apparently bind to the cardiomyocyte surface, as we assessed in experiments using fluorescein isothiocyanate (FITC)-conjugated BAG3 (FIG. 3A). Therefore we investigated whether BAG3 could interact with blood cells. Indeed, we found that FITC-BAG3 bound to macrophages of the cell line J774 (FIG. 3B). BAG3 binding to macrophages was specifically impaired by competing BAG3 peptides or by BAG3-sequestering F(ab')2 fragments from anti-BAG3 monoclonal antibodies (Table I). In particular J774 cells were incubated with 14 nM FITC-BAG3 protein and with 625 nM of BAG3 peptides (peptide 1, peptide 2, peptide 3, peptide 4 or scrambled peptide) or with 420 nM of F(ab')2 fragments from anti-BAG3 monoclonal and polyclonal antibodies (mouse monoclonal AC1, AC2 and rabbit polyclonal TOS2). F(ab')2 fragments from mouse IgG or F(ab')2 fragments from rabbit IgG were used as a negative control.

TABLE I

| | FITC-rBAG3 | FITC-BSA | Competiton assays | |
|---|---|---|---|---|
| | % of positive cells (±S.D.) | % of positive cells (±S.D.) | % of positive cells (±S.D.) | % inhibition |
| FITC-rBAG3 | 15.7 (±0.45) | | | |
| FITC-BSA | | 4.04 (±0.06) | | |
| (FITC-rBAG3)- (FITC-BSA) | 11.06 (±0.45) | | | |
| FITC-rBAG3 + Pep1 | | | 0.18 (±0.05) | 98.4 |
| FITC-rBAG3 + Pep2 | | | 1.21 (±0.63) | 89.1 |
| FITC-rBAG3 + Pep3 | | | 5.86 (±0.43) | 47.2 |
| FITC-rBAG3 + Pep4 | | | 0.68 (±0.20) | 93.8 |
| FITC-rBAG3 + Pep Scr | | | 12.1 (±0.21) | 0.0 |
| FITC-rBAG3 + Mouse IgG F(ab')2 | | | 12.3 (±0.40) | 0.0 |
| FITC-rBAG3 + Rabbit IgG F(ab')2 | | | 14.7 (±0.20) | 0.0 |
| FITC-rBAG3 + AC1 IgG F(ab')2 | | | 4.11 (±0.26) | 62.8 |
| FITC-rBAG3 + AC2 IgG F(ab')2 | | | 3.76 (±0.43) | 66.0 |
| FITC-rBAG3 + TOS2 IgG F(ab')2 | | | 3.19 (±0.21) | 71.1 |

To explore functional consequences of BAG3 binding to macrophages, we tested the effect of recombinant BAG3 on the expression of inducible nitric oxide synthase (iNOS) and cyclooxygenase (Cox)-2 in the cells. As shown in FIG. 3C panel a the levels of those enzymes were enhanced in BAG3-treated macrophages. Furthermore, BAG3 induced the release of nitrite and interleukin (IL)-6 (FIG. 3C panels b and c) confirming that macrophages were activated in response to their binding to the protein.

In sera from CHF patients we could detect significant amounts of anti-BAG3 antibodies (FIG. 2A,B). Autoantibodies production is likely related to the extracellular release of a normally intracellular protein, as happens, for example, in chronic ischaemia patients who produce anti-troponin autoantibodies. ELISA values of anti-BAG3 antibodies in CHF patients' sera are significantly higher than those detected in healthy controls' sera.

Therefore, production of anti-BAG3 antibodies, detected by ELISA, appears a biomarker of chronic heart failure. Its utility for risk stratification and therapy monitoring is worthy of investigation.

BAG3 release by stressed cardiomyocytes and subsequent activation of macrophages, leading to local release of NO, might constitute a protective circuit in heart ischemia.

Indeed, vasodilation, neoangiogenesis and remodelling might be targeted. BAG3 release and its transient or chronic effects deserve investigation and could contribute to our understanding of ischemia and other heart stress states.

Furthermore, BAG3-specific mouse monoclonal antibodies AC-1, AC-2 and AC-3 and/or others or same modified as F(ab), F(ab')2, F(ab) or humanized; or peptides comprising sequences PEP 1 to 4 and/or others are molecules able to bind and/or block soluble BAG3 effects to be used for therapy of inflammatory, oncologic or other diseases involving macrophage activation.

Example 4

BAG3 Expression in PDAC by Immunohistochemistry.

Figure 4A:
FIG. 4A.

We have developed an immunohistochemistry (IHC) kit, including our anti-BAG3 monoclonal antibodies and able to detect BAG3 protein by immunohistochemistry (IHC). This kit revealed BAG3 expression in all the 346 (100%) PDAC biopsies that we analyzed. BAG3 staining revealed a moderate positivity of Langerhans islets, while normal pancreatic ducts and pancreatic acinar cells had no BAG3 expression. This was true in both normal pancreas and non-neoplastic pancreatic tissue adjacent to the tumor mass. BAG3 staining was observed predominantly in the cytoplasm of tumor cells. The intensity of staining of BAG3 was variable as was the number of positive cancer cells. Furthermore, Langerhans insulae were positive and constituted a good internal control of IHC (FIG. 4A). Therefore our kit allows the detection of BAG3 protein in PDAC by IHC. Furthermore, it allows detecting BAG3 protein by IHC also in other tumour or normal tissues We investigated also the expression of BAG3 in correlation with patients' survival and in response to therapy. We analyzed a cohort of 346 PDAC samples from the same number of patients (Table II) describing data of all tumour samples analyzed by immunohistochemistry and data of the subgroup of R0 patients analyzed with survival data; We assigned a score based on the proportion of positive cancer cells in the sample by counting the number of positive cells over the total cancer cells in 10 non-overlapping fields using a 400× magnification.

Figure 4B:
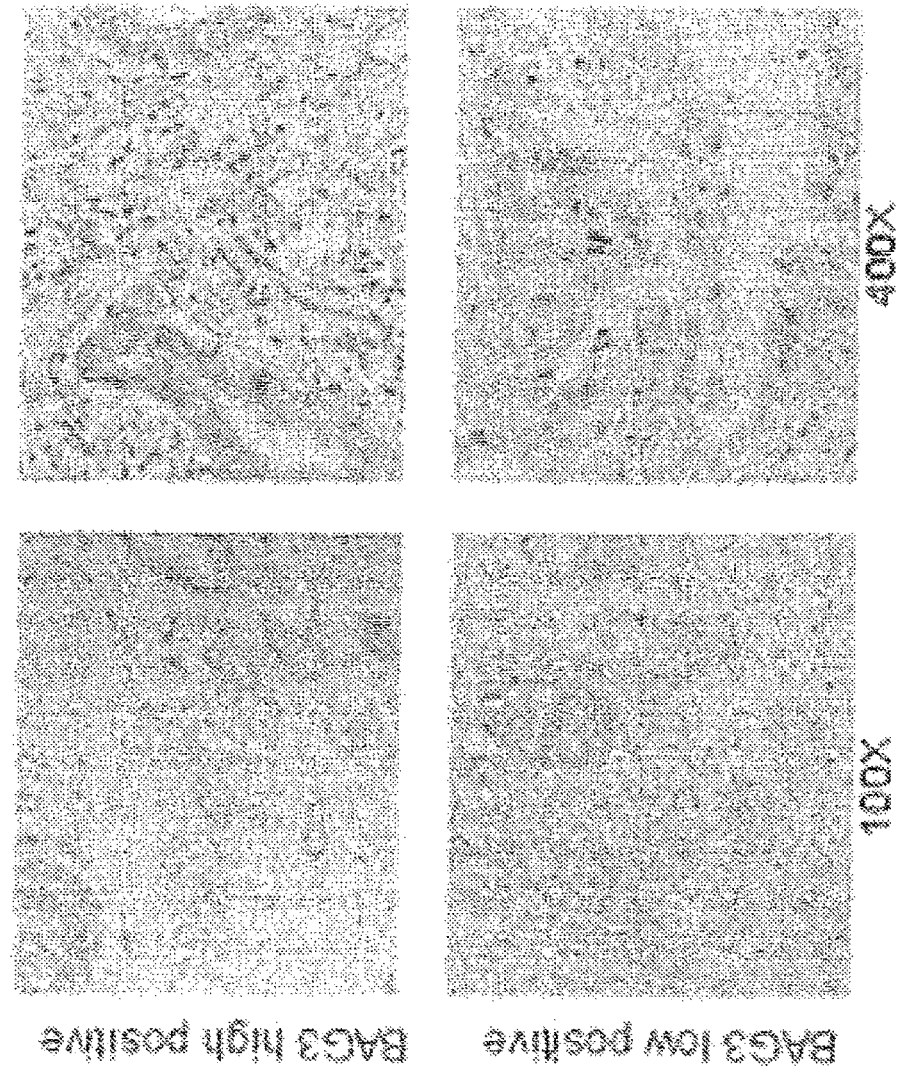
Figure 4C:
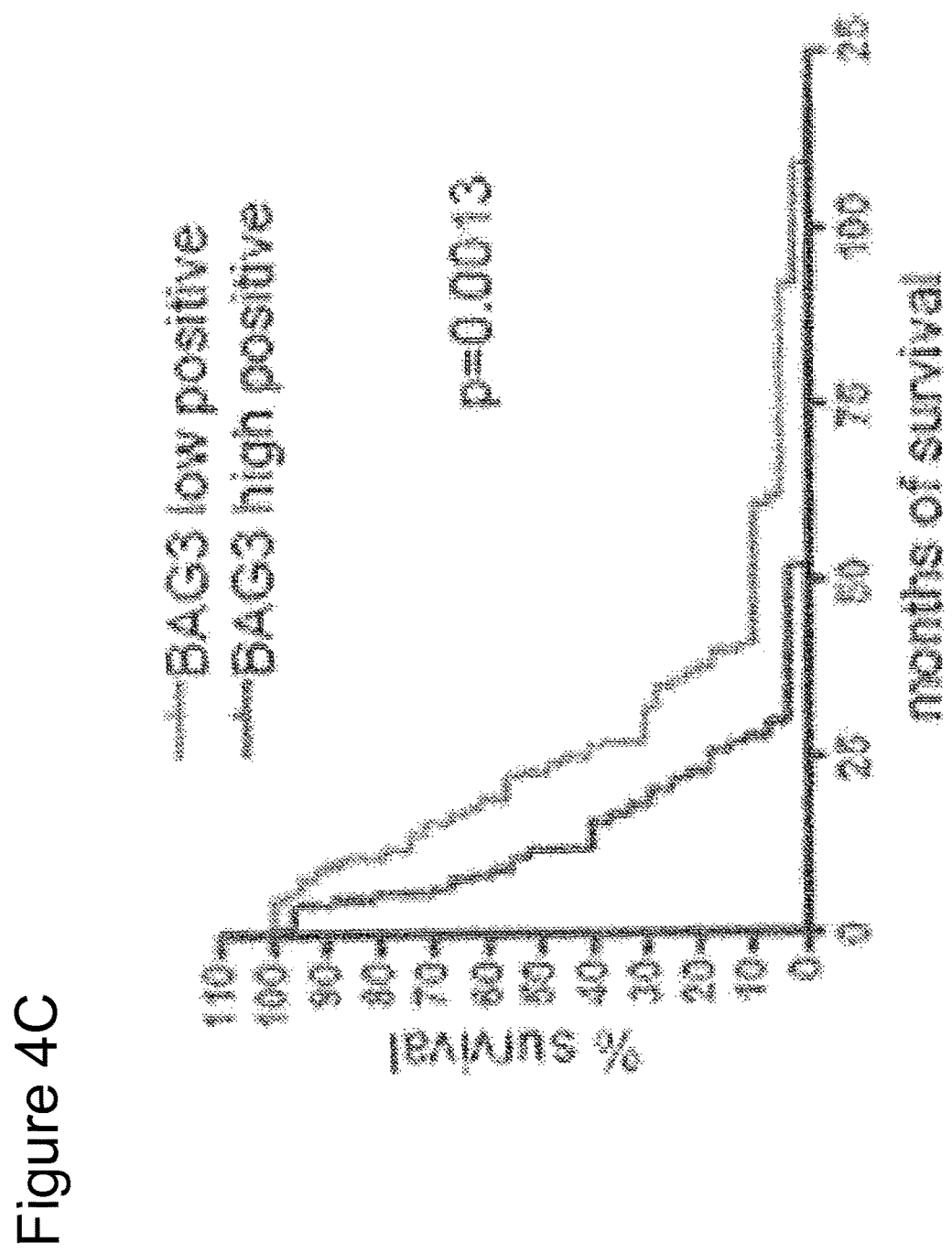

The median percentage of BAG3 positive cells, calculated as described, was 40% and this value was used as a cut-off to separate low and high positive samples. Based on this classification 190 patient samples (55%) were classified as low positive (≤40% of positive cells), and 156 (45%) were classified as high positive (>40% of positive cells) (FIG. 4, panel B). The survival analysis was performed in a cohort of 66 patients of which all the lesions examined were with resection margins free from tumor cells (R0) and only the 3.7% showed the presence of metastases to distant organs (Table II). Obtained data showed that patients with high BAG3 expression had a significantly shorter survival (median survival=12.0 months) than those with low BAG3 expression (median survival=23.0 months), (p=0.0013) (FIG. 4, panel C). Based on Cox proportional analysis high BAG3 expression was associated with a more than two-fold higher risk of death (Table III).

TABLE III

| Parameter | HR | 95% CI | p-value |
|---|---|---|---|
| Age (years) | 0.99 | 0.97-1.02 | 0.601 |
| Sex (M vs. F) | 0.86 | 0.48-1.55 | 0.617 |
| Tumor grade (G2 vs. G1) | 0.84 | 0.24-2.98 | 0.789 |
| Tumor grade (G3 vs. G1) | 1.55 | 0.45-5.37 | 0.486 |
| Local tumor stage (T3 vs. T2) | 2.5 | 0.30-21.17 | 0.400 |
| Nodal stage (N1 vs. N0) | 1.17 | 0.58-2.37 | 0.668 |
| BAG3 Positivity (High vs. Low) | 2.7 | 1.53-4.78 | <0.001 |
| | | events = 66 n = 66 | |

Example 5

BAG3 Protein in Response to Therapy

The first-line chemotherapy for treatment of pancreatic cancer is gemcitabine. In order to investigate the role of BAG3 protein in response to therapy, we analyzed the effect of BAG3 down-modulation in human PDAC cells. We transfected the cells with a specific siRNA targeting bag3 mRNA or with a non specific (NT) siRNA, and treated cells with gemcitabine for the indicated times. Silencing of BAG3 enhanced cell apoptosis in response to the drug (FIG. 8).

These results demonstrate the over expression of BAG3 protein and mRNA in pancreatic adenocarcinoma and the association of high expression levels with a higher risk of death, assigning to BAG3 a role of marker useful for prognosis and therapy choice. Furthermore they show that BAG3 down-modulation enhances apoptosis in PDAC cells. Due to its wide expression in all the lesions tested and to its involvement in sustaining pancreatic cancer cell survival, BAG3 represents a valuable target for innovative therapies in PDAC.

Example 6

BAG3 Protein in Sera of Pancreatic Cancer Patients

Because of its wide expression in pancreatic cancer patients, we investigated whether BAG3 was present in sera

TABLE II

| | No. | age | sex | | Local tumor stage T (%) | | | | Nodal stage N (%) | | Tumor grade G (%) | | |
|---|---|---|---|---|---|---|---|---|---|---|---|---|---|
| | Tot | average ± S.D. | M | F | T1 | T2 | T3 | T4 | N0 | N1 | G1 | G2 | G3 |
| PDAC patients data | 346 | 63.0 ± 10.5 | 181 | 165 | 5 (1.4) | 59 (17.1) | 264 (76.3) | 18 (5.2) | 130 (37.6) | 216 (62.4) | 16 (4.6) | 177 (51.2) | 153 (44.2) |
| PDAC patients with survival data | 66 | 61.9 ± 11.3 | 36 | 30 | 0 (0.0) | 1 (1.5) | 65 (98.5) | 0 (0.0) | 13 (19.7) | 53 (80.3) | 3 (4.5) | 37 (56.1) | 26 (39.4) | of pancreatic cancer patients. We found that indeed BAG3 was detectable. Also anti-BAG3 antibodies were detectable, although in prevalence complexed with BAG3. We therefore developed an ELISA test for detecting BAG3/antibody complexes. We analyzed sera from 51 healthy donors and 55 patients affected by PDAC (Table IV).

TABLE IV

|  | N (TOT) | AGE (median + s.e.) | M | F |
| --- | --- | --- | --- | --- |
| healthy donors | 51 | 58.7 + 1.6 | 35 | 16 |
| PDAC patients | 55 | 64.0 + 1.3 | 30 | 25 |

As shown in FIG. 9A, immunocomplexes (measured in arbitrary units) were significantly higher in sera from patients that in those from healthy donors. Furthermore ROC analysis of ELISA test results, using as cut-off 0.183 A.U., in 65% sensitivity and 78% specificity (FIG. 9B).

Example 7

BAG3 Expression by Quantitative Real-Time PCR

The immunohistochemical data on BAG3 expression was also confirmed measuring bag3 mRNA levels in 25 PDAC tissue samples (Table V).

TABLE V

| No. Tot | age average + S.D. | sex | | Local tumor stage T (%) | | | | Nodal stage N (%) | | Tumor grade G (%) | | |
| --- | --- | --- | --- | --- | --- | --- | --- | --- | --- | --- | --- | --- |
|  |  | M | F | T1 | T2 | T3 | T4 | N0 | N1 | G1 | G2 | G3 |
| 25* | 65.4 ± 11.9 | 21 | 4 | 2 (8.0) | 3 (12.0) | 20 (80.0) | — | 6 (24.0) | 19 (76.0) | 3 (12.5) | 13 (54.2) | 8 (33.3) |

Figure 7A:
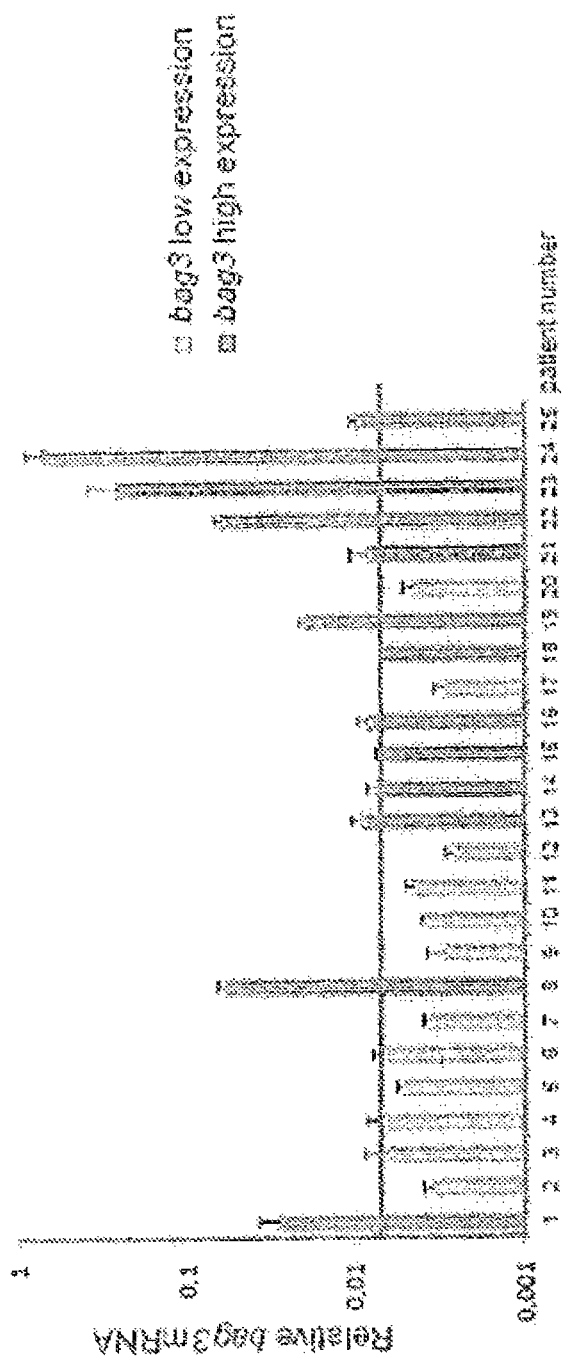
Figure 7B:
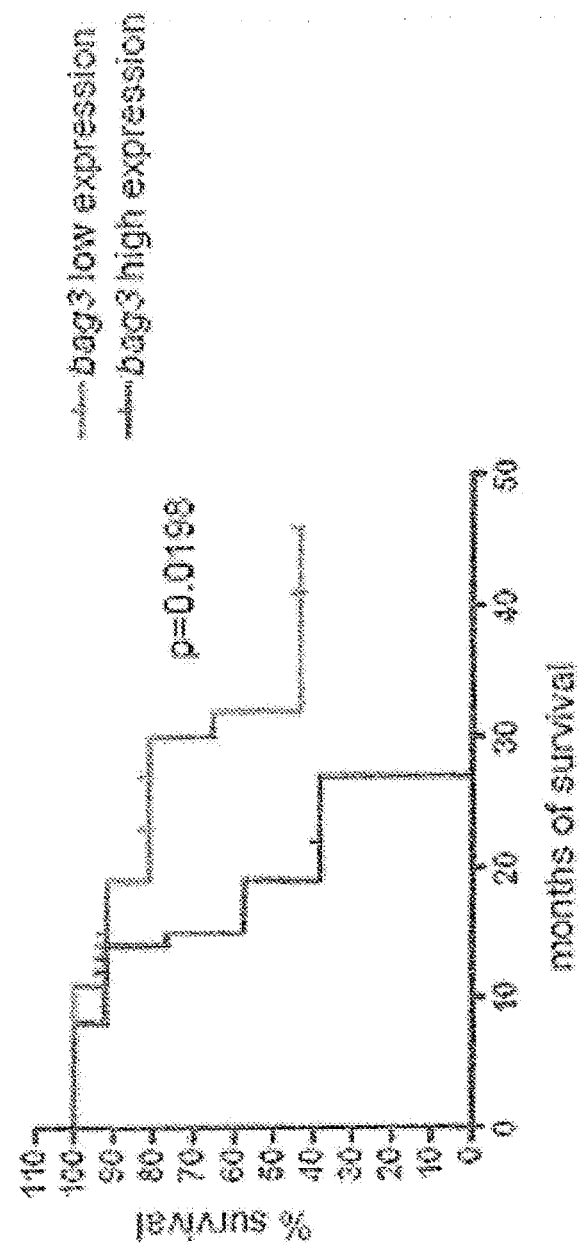
Figure 8A:
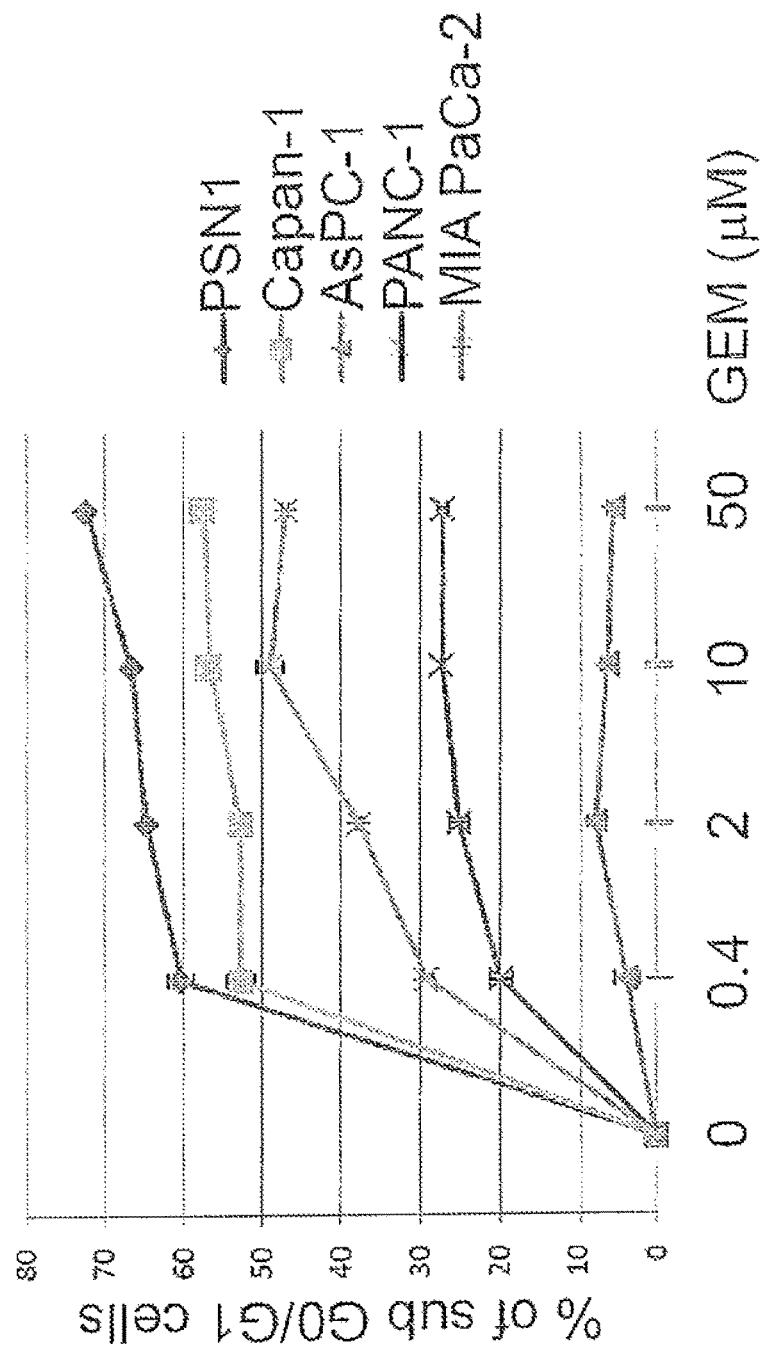
Figure 8B:
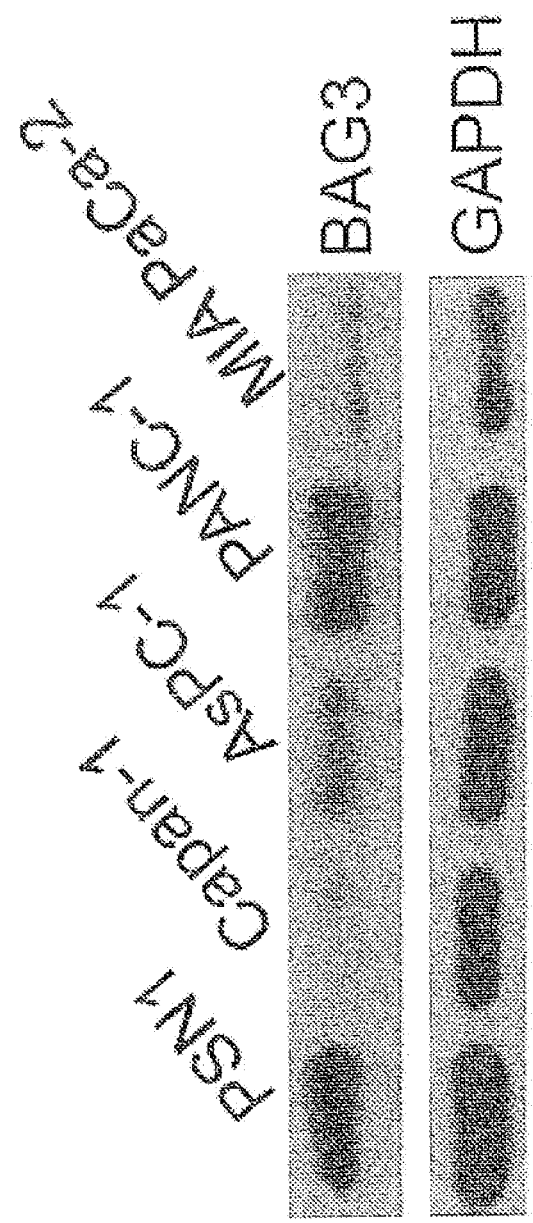
Figure 8C:
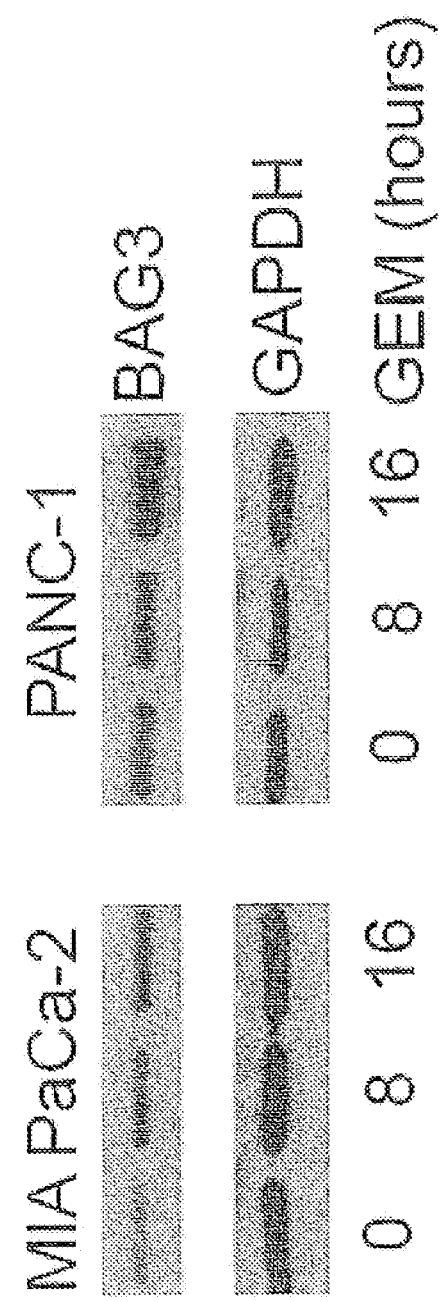
Figure 8D:
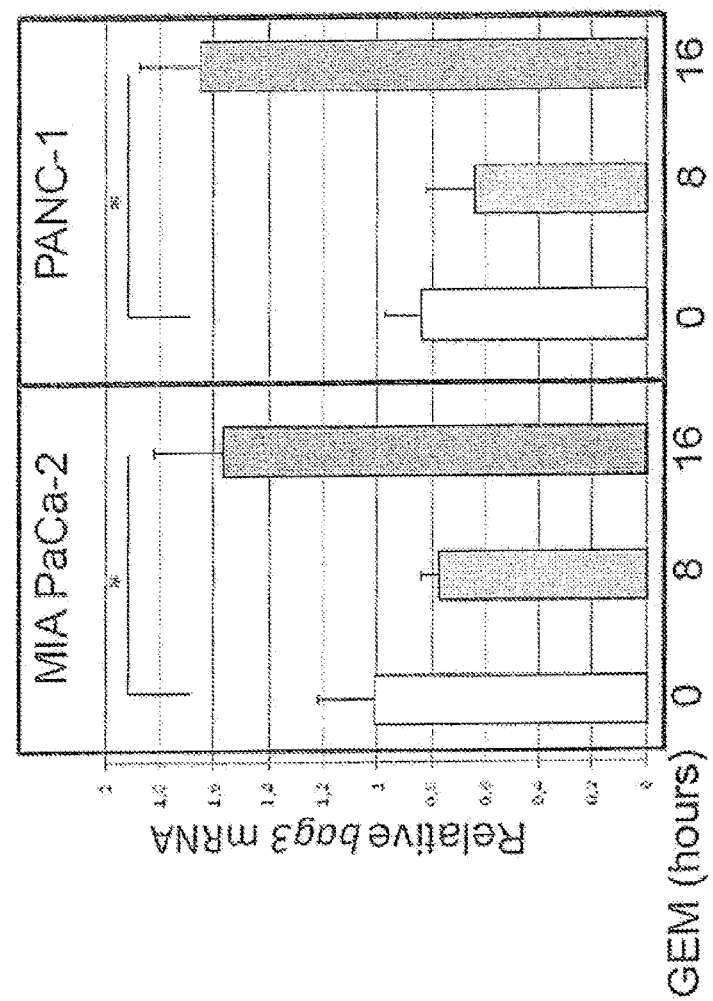
Figure 8F:
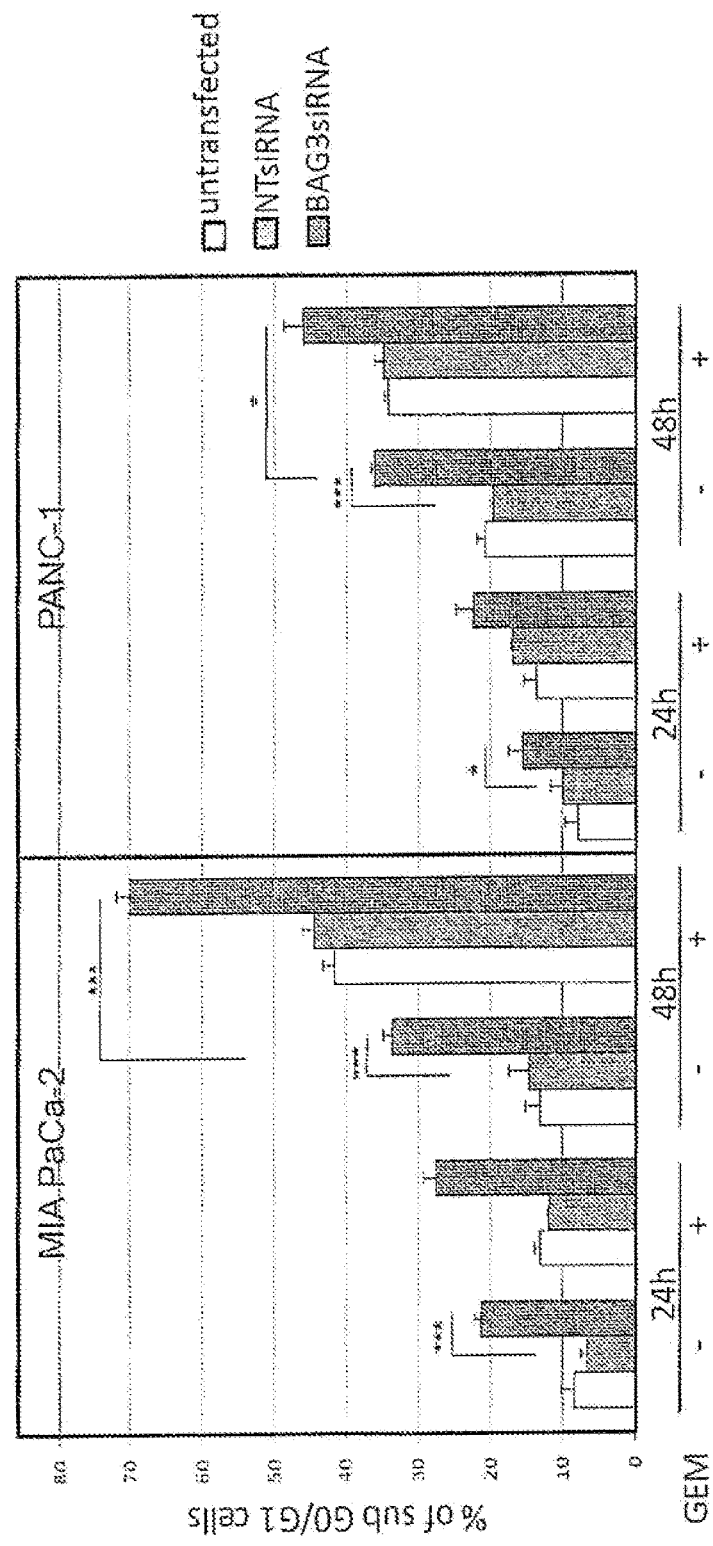

In particular, there were 16 survivors out of the 25 patients, while 9 patients died of pancreatic cancer progression, at the time of the analysis. The median of expression of bag3 mRNA in tumors analyzed was set at 0.0068 (Q1=0.004; Q3=0.010) (FIG. 7, panel A). All the considered demographics and clinical features of PDAC patients were unrelated to bag3 mRNA levels. Thus, correlation with survival was evaluated and the median of bag3 expression levels in PDAC samples was used as a cut-off to separate patients with low from those with high bag3 expression. Thirteen samples (52%) were thus classified as high bag3 positive and 12 samples (48%) as low bag3 positive. Patients with high bag3 expression had shorter survival (median survival=19.0 months) than those with low bag3 expression (median survival=32.0 months), p-value=0.0198 (FIG. 7, panel B). Based on Cox proportional analysis high bag3 expression was associated with over six fold higher risk of death (univariate: HR=6.094; 95% CI=1.105-33.597, p=0.038).

bag3 primers that detect BAG3 expression by quantitative real-time RT-PCR. We developed a RT-PCR kit containing specific primers for bag3 mRNA detection and quantification.

Example 8

We evaluated BAG3 antibodies levels prior to diagnosis of PDAC in a case control study set within the prospective biobank derived from UKCTOCS (Menon et al., BMJ, 337:a2079, 2008). The trial cohort of 202,000 postmenopausal women donated a single serum at recruitment and 50,000 women continued to donate serum samples annually. Women diagnosed with pancreatic cancer post-randomisation were identified by cancer registry data and postal follow up questionnaires.

For these women diagnosed for PDAC we obtained sera samples at different time points prior PDAC diagnosis. Control sera were obtained from healthy subjects and we measure BAG3 antibody titers in about five control subjects compared to each PDAC case. Furthermore, control sera came from subjects age matched with the respective PDAC case. This control sera matching was used for each time point.

Detection of BAG3-specific antibodies in patients sera from 49 female subjects at 0-1 years pre diagnosis for pancreatic adenocarcinoma were compared with sera from 235 female control subjects sera for the presence of BAG3 specific antibodies in a specific ELISA test.

BAG3 antibodies concentrations were detected in a specific ELISA assay.

As shown in FIG. 10, BAG3 antibodies were significantly higher in cases at least 3-4 years pre-diagnosis in respect to control subjects.

Others time points included: 53 subjects at 1-2 years pre diagnosis for PDAC compared to 251 controls; 44 subjects at 2-3 years pre diagnosis for PDAC compared to 212 controls; 42 subjects at 3-4 years pre diagnosis for PDAC compared to 187 controls.

As shown in FIG. 10, BAG3 antibodies were significantly higher in cases at least 3-4 years pre-diagnosis in respect to control subjects.

Methods

Cell Cultures

HCMa (Human Cardiac Myocytes-adult) were purchased from Sciencell Research Laboratories (San Diego, Calif.) and grown in Cardiac Myocyte Medium (CMM, FBS 5%, Cardiac Myocyte Growth Supplement 1%, penicillin/streptomycin solution 1%) (Sciencell Research Laboratories, San Diego, Calif.). All experiments were performed on low-passage cell cultures. Embryonic rat cardiomyoblasts (line H9c2) was purchased from the American Type Culture Collection (ATCC, Manassas, Va., USA) and grown in Dulbecco's Modified Eagle's Medium (DMEM) supplemented with 10% fetal bovine serum (FBS), 100 U/mL penicillin and 100 µg/mL streptomycin. J774A.1, murine monocyte macrophage cell line (ATCC, Manassas, Va., USA), was grown in DMEM supplemented with 10% fetal bovine serum (FBS), 25 mM HEPES, 2 mM glutamine, 100 u/mL penicillin and 100 µg/mL streptomycin.

The pancreatic cancer cell lines (MIA PaCa-2, AsPC-1, PSN1, Capan-1 and PANC-1) were received from the American Type Culture Collection (ATCC; Manassas, Va.) cell bank. MIA PaCa-2 cells were cultured in Dulbecco's Modified Eagle's Medium (DMEM) and supplemented with 10% FBS and 2.5% horse serum. AsPC-1 and PSN1 cells were grown in RPMI-1640 Medium supplemented with 10% FBS. Capan-1 were cultured in RPMI-1640 containing 20% FBS while PANC-1 were cultured in DMEM supplemented with 10% FBS. All media for the above cell lines were purchased from BioWhittaker-Lonza (Bergamo, Italy) MediaTech (Manassas, Va.) and were supplemented with 100 units of penicillin/mL and 2 μg streptomycin/mL (Sigma-Aldrich, St. Louis, Mo.). The cells were incubated at 37° C. in a 5% $CO_2$ environment. Cells were treated with Gemcitabine (2',2'-difluorodeoxycytidine; GEM, Gemzar®) provided by Eli Lilly (Sesto Fiorentino, Italy) at the indicated concentrations.

Dissociation of BAG3 Antibodies in Human Sera

Sera were diluted 1:40 with dissociation buffer (PBS with 1.5% BSA and 0.2 M glycine-acetate pH 2.5) to a 500 μl final volume and incubated for 20 min at room temperature. The sera were then pipetted into the sample reservoir of Microcon centrifugal filter device, YM-100 (100,000 MW cut-off; Millipore, Billerica, Mass., USA) and centrifuged at 14,100 rpm for 20 min at room temperature. The sample reservoir was then separated from the flow through, placed inverted into a second tube and centrifuged at 5,000 rpm for 3 min at room temperature. The collected solution containing the antibody dissociated was adjusted to pH 7.0 with 1 M Tris buffer, pH 9.0. The retentate volume was reconstituted to the initial volume (500 pl) with dilution buffer (PBS with 1.5% BSA and 0.1% Tween-20).14 For detection of BAG3 protein by immunoblotting, the dissociated antibodies were diluted 1:200 in TBST containing 5% bovine serum albumin overnight at 4° C.

Western Blot Analysis

Cells were harvested and lysed in a buffer containing 20 mM HEPES (pH 7.5), 150 mM NaCl, 0.1% Triton (TNN buffer) supplemented with a protease inhibitors cocktail (1 mM phenylmethylsulfonyl fluoride, 1 mg/ml pepstatin A, 2 mg/ml aprotinin) by 3 cycles of freezing and thawing. Soluble proteins were collected after a centrifugation at 10,000 g for 15 min and their amount was determined by Bradford assay (Bio-Rad, Hercules, Calif.). 25 μg of total protein and serum samples (1:2 in PBS-T 0.05%) were run on 8% or 10% SDS-PAGE gels and electrophoretically transferred to nitrocellulose membrane. Nitrocellulose blots were blocked with 10% non-fat dry milk in TBST buffer (20 mM Tris-HCl pH 7.4, 500 mM NaCl, and 0.1% Tween 20) and incubated with primary antibodies in TBST containing 5% bovine serum albumin or 5% non-fat dry milk, overnight at 4° C. Immunoreactivity was detected by sequential incubation with horseradish peroxidase-conjugated secondary antibodies purchased from Pierce (Rockford, Ill.) and ECL detection reagents purchased from Amersham Life Sciences Inc. (Arlington Heights, Ill., USA).

Scanning densitometry of the bands was performed with an Image Scan (SnapScan 1212; Agfa-Gevaert NV). The area under the curve related to each band was determined using Gimp2 software. Background was subtracted from the calculated values.

Mass Spectrometry

Protein bands were excised and gel pieces were subsequently washed with MilliQ Water and Acetonitrile and the proteins were digested in situ as described in Shevchenko protocol. Briefly, gel slices were reduced in 1,4-dithiothreitol (10 mM) and alkylated with iodoacetamide (50 mM), then washed and rehydrated in trypsin solution (12 ng/μL) on ice for 1 h. After the addition of 30 μL ammonium bicarbonate (10 mM, pH 7.5), samples were digested overnight at 25° C. 5 μL of the obtained peptide mixture were injected onto a nano Acquity LC system (Waters Corp. Manchester, United Kingdom). The peptides were separated on a 1.7 μm BEH C-18 column (Waters Corp. Manchester, United Kingdom) at a flow rate of 200 nl/min. The gradient (Solution A: 0.1% formic acid, solution B: 0.1% formic acid, 100% ACN) started at 5% and ended at 50% B after 55 min. MS and MS/MS data were acquired using a Q-TOF Premier mass spectrometer (Waters Corp., Micromass, Manchester, United Kingdom). Doubly and triply charged peptide-ions were automatically chosen by the MassLynx software and fragmented. MS data were automatically processed and peaklists for protein identifications by database searches were generated by the ProteinLynx software. Database searches were carried out with MASCOT server using the SwissProt protein database. The SwissProt human database (405506 sequences; 146166984 residues) was searched allowing 1 missed cleavage, carbamidomethyl (C) as fixed modification. The peptide tolerance was set to 60 ppm and the MS/MS tolerance to 0.8 Da.

Purification of Exocytic Vesicles by Differential Ultracentrifugation

Serum-free medium of H9c2 was cleared of cells and large debris by serial centrifugation at 4° C. (2000×g for 15 min, 10,000×g for 30 min). After each of the first two centrifugations, pellets are discarded, and the supernatant is kept for the next step. The final supernatant is then ultracentrifuged at 150,000×g for 90 min at 4° C. (with a SW50.1 rotor, and an Optima L-90K Ultracentrifuge, Beckman Coulter) to pellet exosomes. The pellet is washed in PBS to eliminate contaminating proteins and centrifuged one last time at 150,000×g for 90 min at 4° C.16 After washing, the pellet (exosomes) was resuspended in 20 μl of PBS and analyzed with the anti-BAG3 TOS-2 polyclonal antibody in comparison with a whole-cell lysate by western blot. Rab-4 was analyzed as a marker for exocytic vesicles.

FACS Analysis rBAG3 binding—J774 A.1 cells were blocked with 2% FBS+0.1% NaN3 in PBS for 15 min on ice and incubated ($2.5 \times 10^5/100$ μl) with different concentration of FITC-rBAG3 protein (7, 14 and 70 nm) or FITC-BSA (70 nM) in PBS containing 2% FBS+0.1% NaN3 for 30 min at 4° C. in the dark. After washing with PBS, the cells were resuspended in PBS+2% FBS+0.1% NaN3 and analyzed with a FACScan (BD Biosciences) flow cytometer.

Competition—J774 A.1 cells ($2.5 \times 10^5/100$ μl) were incubated with 625 nM of BAG3 peptides (peptide 1, peptide 2, peptide 3, peptide 4 or scrambled peptide) or with 420 nM of F(ab')2 fragments from anti-BAG3 monoclonal and polyclonal antibodies (mouse monoclonal AC1, AC2 and rabbit polyclonal TOS2) or F(ab')2 fragments from mouse IgG or F(ab')2 fragments from rabbit IgG in PBS containing 2% FBS+0.1% NaN3 for 30 min on ice. After incubation the cells were washing with PBS and then were incubated with of FITC-rBAG3 protein (14 nM), in PBS containing 2% FBS+0.1% $NaN_3$ for 30 min at 4° C. in the dark. After washing with PBS, the cells were resuspended in PBS+2% FBS+0.1% NaN3 and analyzed by flow cytometer (BD Biosciences).

IL6 Detection by ELISA

IL6 was measured in supernatant of J774 A.1 cells ($5 \times 10^4$/in 96-well microplates) treated with LPS (10 ng/ml) or with rBAG3 (14 nM) or BSA (14 nM) for 10 or 20 hours in absence or presence of polymyxin B sulfate (5 μg/ml). After treatment 50 μL of cell culture medium were collected and analyzed in triplicate with a mouse IL6 Kit (eBioscience).

Fluorescence

Cells were cultured on coverslips in six-well plates to 60-70% confluence and equal amount of rBAG3-FITC and BSA-FITC proteins were added in HCMa and J774 A1 culture media with 0.1% $NaN_3$ for 1 h. Coverslips were washed in 1×PBS and fixed in 3.7% formaldehyde in 1×PBS for 30 min at room temperature, and then incubated for 5 min with 1×PBS 0.1M glycine. Following incubation with a 1:100 dilution of anti-β-integrin monoclonal antibody at 4° C., coverslips were washed three times with 1×PBS. After incubation with a 1:500 dilution of goat anti-mouse IgG DyLight 594-conjugated antibodies (Jackson ImmunoResearch, West Grove, Pa., USA) at room temperature for 45 min, coverslips were again washed for three times in 1×PBS. Once incubation with Hoechst 33342 (Sigma Aldrich, 2 μg/ml) at room temperature for 10 min, coverslips were again washed for 3 times in PBS and then in distilled water. The coverslips were then mounted on a slide with interspaces containing 47% (v/v) glycerol. Samples were analyzed using a confocal laser scanning microscope (Zeiss LSM confocal microscope, Germany). Images were acquired in sequential scan mode by using the same acquisitions parameters (laser intensities, gain photomultipliers, pinhole aperture, objective 63×, zoom 2) when comparing experimental and control material. For production of figures, brightness and contrast of images were adjusted by taking care to leave a light cellular fluorescence background for visual appreciation of the lowest fluorescence intensity features and to help comparison among the different experimental groups. Final figures were assembled using Adobe Photoshop 7 and Adobe Illustrator 10. Leica Q9 Confocal Software and ImageJ were used for data analysis.

Measurement of Antibody titers by ELISA

NUNC Maxisorp 96 well ELISA plates were coated with recombinant BAG3 protein 1 μg/ml (50μl/well) in PBS, pH 7 and incubated overnight at 4° C. Plates were washed 2 times with washing buffer (PBS+0.05% Tween-20), and then blocked (150 μl/well) for one hour at room temperature with 0.5% fish gelatin in PBS. Following blocking, the plates were washed 2 times with washing buffer and sera were diluted 1:70 with 0.5% fish gelatin in washing buffer and then applied (50 μl/well) in triplicate and incubated at room temperature for two hour. The plates were then washed 6 times with washing buffer. Anti-human IgG (H+L) antibody (Sigma Aldrich) was diluted 1:20,000 with 0.5% fish gelatin in washing buffer, added at 50 μl/well and incubated at 4° C. for 30 minutes. After incubation, the plates were washed 6 times, developed with TMB (50 μl/well) (eBioscience), the reaction stopped with 4.5 M sulfuric acid (25 μl/well) and the plates were analyzed spectrophotometrically at 450 nm.

$NO_2^-$ Assay

Nitrite content ($NO_2^-$), a stable metabolite of NO released by cells in the culture supernatant, was measured in J774 A.1 cells (5×10$^4$/in 96-well microplates) treated with LPS (10 ng/ml) or with rBAG3 (7, 14 and 28 nM) or BSA (28 nM) for 24 hours in absence or presence of polymyxin B sulfate (Sigma-Aldrich, St. Louis, Mo., USA) 5 μg/ml. NO2$^-$ amounts were measured by Griess reaction. Briefly, 100 μL of cell culture medium were mixed with 100 μL of Griess reagent—equal volumes of 1% (w:v) sulphanilamide in 5% (v:v) phosphoric acid and 0.1% (w:v) naphtylethylenediamine-HCl—and incubated at room temperature for 10 min, and then the absorbance was measured at 550 nm in a microplate reader Titertek (Dasit, Cornaredo, Milan, Italy). The amount of NO2- (as μM) in the samples was calculated from a sodium nitrite standard curve.

Measurement of BAG3/Antibody Immunocomplexes by ELISA

NUNC Maxisorp 96 well ELISA plates were coated with anti-BAG3 monoclonal antibody AC-1, AC-2 or AC-3 in PBS, pH 7 and incubated overnight at 4° C. Plates were washed 2 times with washing buffer (PBS+0.05% Tween-20), and then blocked (150 μl/well) for one hour at room temperature with 0.5% fish gelatin in PBS. Following blocking, the plates were washed 2 times with washing buffer and sera were diluted 1:70 with 0.5% fish gelatin in washing buffer and then applied (50 μl/well) in triplicate and incubated at room temperature for two hour. The plates were then washed 6 times with washing buffer. Anti-human IgG (H+L) antibody (Sigma Aldrich) was diluted 1:20,000 with 0.5% fish gelatin in washing buffer, added at 50 μl/well and incubated at 4° C. for 30 minutes. After incubation, the plates were washed 6 times, developed with TMB (50 μl/well) (eBioscience), the reaction stopped with 4.5 M sulfuric acid (25 μl/well) and the plates were analyzed spectrophotometrically at 450 nm.

Immunohistochemistry

Immunohistochemistry protocol included: deparaffination in xylene, re-hydration through descending concentrations of alcohol up to pure water, non-enzymatic antigen retrieval in citrate buffer, pH 6.0, for 30 minutes at 95° C., and endogenous peroxidase quenching with H2O2 in methanol for 20 minutes. After rinsing with PBS, the samples were blocked with 5% normal horse serum in 0.1% PBS/BSA. To detect BAG3, samples were incubated for 1 hour at room temperature with BAG3 monoclonal antibody AC-1, AC-2 or AC-3 at the concentration of 3 μg/ml. After washing thoroughly with PBS, sections were incubated with a biotinylated secondary anti-mouse IgG for 20 minutes, then rinsed, incubated with avidin-biotin-complexes peroxidase (purchased from Novocastra-Leica Microsystems, Milano, IT) and developed with diaminobenzidine (Sigma-Aldrich, St. Louis, Mo.). Finally, the sections were counterstained with hematoxylin, dehydrated in alcohol, cleared in xylene, and mounted with Permount (Fisher Scientific, Milan, IT).

Quantitative Real-Time RT-PCR

Tissue specimens of resected pancreatic cancer were taken, immediately frozen in liquid nitrogen, and stored at −80° C. until RNA extraction. Total RNA was isolated from frozen tissues and from pancreatic cancer cell lines by means of phenol extraction (TRIzol Reagent, Invitrogen Corporation, Carlsbad, Calif., USA). In tissue samples Cancer cellularity was enriched by cryostat sectioning and dissection of most cellular areas. RNA concentration and purity (A260:A280>2.0; A260/A230>1.8) were validated by NanoDrop Spectrophotometer (Thermo Fisher, Waltham, Mass., USA). 1.0 μg of total RNA was reverse-transcribed using the High-Capacity cDNA Reverse Transcription Kit according to the manufacturer's instructions (Applied Biosystems, Applera, Foster City, Calif., USA). Quantitative real-time PCR assay was used to assess the differential expression of BAG3 in tumor tissue samples. Primers for the human bag3 gene were synthesized by Primm srl (Milano, Italy) (forward primer: (SEQ ID NO:16) CCT GTT AGC TGT GGT TG; reverse primer: (SEQ ID NO:17) AAC ATA CAG ATA TTC CTA TGG C). All qPCRs were performed in a 25-μl final volume, in three replicates per sample, by using QuantiFast SYBR Green PCR kit (QIAGEN, Hamburg, Germany) and run in an ABI PRISM® 7700 Sequence Detection System (Applied Biosystems, Applera, Foster City, Calif., USA) according to the following conditions: 95° C. for 5 min, 40 cycles at 95° C. for 10 s and at 60° C. for 30 sec. Data were acquired as threshold cycle (Ct) value using the S.D.S software v 2.1. In each sample, bag3 mRNA relative expression levels was obtained using the comparative method, after normalizing for the expression of the endogenous GAPDH.

From the above description and the above-noted examples, the advantage attained by the biological markers described and obtained according to the present invention are apparent.

What is claimed is:

1. A method for detecting the level of an immune complex of an anti-BAG3 autoantibody bound to soluble BAG3 (Bcl2-associated athanogene 3) in a biological sample, comprising:
   a. obtaining a biological sample from serum, plasma, urine, or saliva of a human;
   b. contacting the biological sample with a microplate coated with an anti-BAG3 antibody to bind the immune complex in the biological sample, if present, to the microplate; and
   c. detecting the level of the bound immune complex with an anti-human IgG antibody.

2. The method according to claim 1, wherein the microplate is coated with an anti-BAG3 antibody AC-1, AC-2, or AC-3.

* * * * *